(12) United States Patent
Uematsu et al.

(10) Patent No.: US 10,857,228 B2
(45) Date of Patent: Dec. 8, 2020

(54) ADJUVANT FOR VACCINES, VACCINE, AND IMMUNITY INDUCTION METHOD

(71) Applicant: The University of Tokyo, Tokyo (JP)

(72) Inventors: Satoshi Uematsu, Tokyo (JP); Naoki Takemura, Tokyo (JP)

(73) Assignee: The University of Tokyo, Tokyo (JP)

( * ) Notice: Subject to any disclaimer, the term of this patent is extended or adjusted under 35 U.S.C. 154(b) by 0 days.

(21) Appl. No.: 15/580,009

(22) PCT Filed: Jun. 10, 2016

(86) PCT No.: PCT/JP2016/067403
§ 371 (c)(1),
(2) Date: Jan. 11, 2018

(87) PCT Pub. No.: WO2016/199904
PCT Pub. Date: Dec. 15, 2016

(65) Prior Publication Data
US 2018/0177867 A1    Jun. 28, 2018

(30) Foreign Application Priority Data

Jun. 10, 2015 (JP) .................. 2015-117871

(51) Int. Cl.
| | | |
|---|---|---|
| A61K 39/39 | (2006.01) | |
| A61K 31/716 | (2006.01) | |
| A61K 38/22 | (2006.01) | |
| A61K 38/19 | (2006.01) | |
| A61K 39/00 | (2006.01) | |
| A61K 45/06 | (2006.01) | |
| A61P 37/04 | (2006.01) | |
| A61K 31/711 | (2006.01) | |

(52) U.S. Cl.
CPC ............ *A61K 39/39* (2013.01); *A61K 31/711* (2013.01); *A61K 31/716* (2013.01); *A61K 38/193* (2013.01); *A61K 38/22* (2013.01); *A61K 39/0005* (2013.01); *A61K 45/06* (2013.01); *A61P 37/04* (2018.01); *A61K 2039/54* (2013.01); *A61K 2039/545* (2013.01); *A61K 2039/55522* (2013.01); *A61K 2039/55561* (2013.01); *A61K 2039/55566* (2013.01); *A61K 2039/55583* (2013.01)

(58) Field of Classification Search
None
See application file for complete search history.

(56) References Cited

U.S. PATENT DOCUMENTS

| | | | | |
|---|---|---|---|---|
| 6,048,536 A * | 4/2000 | Chatfield | ............. | A61K 39/145 424/206.1 |
| 9,694,070 B2 * | 7/2017 | Gorden | .................. | A61K 39/39 |
| 9,885,017 B2 * | 2/2018 | Dutartre | ................. | A61K 39/29 |
| 10,093,701 B2 * | 10/2018 | Stone | ................... | C07K 14/705 |
| 10,117,915 B2 * | 11/2018 | Bellgrau | .......... | A61K 39/39541 |
| 10,391,167 B2 * | 8/2019 | Fukasaka | ................. | C12N 7/00 |
| 2008/0145375 A1 | 6/2008 | Bembridge et al. | | |
| 2008/0233140 A1 | 9/2008 | Banchereau et al. | | |
| 2012/0244155 A1 * | 9/2012 | Lecine | ................... | C07K 16/28 424/134.1 |
| 2013/0323814 A1 * | 12/2013 | Ozawa | ................. | C12N 9/0069 435/189 |
| 2014/0199379 A1 | 7/2014 | Tartour et al. | | |
| 2014/0234377 A1 | 8/2014 | Okazaki et al. | | |
| 2014/0314804 A1 * | 10/2014 | Gorden | .................. | A61K 39/39 424/193.1 |
| 2014/0322214 A1 * | 10/2014 | Banchereau | ......... | A61K 39/395 424/134.1 |
| 2016/0208260 A1 | 7/2016 | Ishii et al. | | |
| 2016/0213773 A1 * | 7/2016 | Fukasaka | ................ | A61K 39/39 |
| 2017/0224811 A1 * | 8/2017 | Van Haren | ............. | A61K 35/74 |
| 2018/0177867 A1 * | 6/2018 | Uematsu | ................ | A61K 38/22 |
| 2019/0022197 A1 * | 1/2019 | Bellgrau | .......... | A61K 39/39541 |

FOREIGN PATENT DOCUMENTS

| | | | | |
|---|---|---|---|---|
| EP | 3048170 A1 | 7/2016 | | |
| EP | 3308800 A4 * | 11/2018 | ............ | A61K 38/22 |
| JP | 2007505827 A | 3/2007 | | |
| JP | 2008127277 A | 6/2008 | | |
| JP | 2009-242367 A | 10/2009 | | |
| JP | 2011057605 A | 3/2011 | | |
| JP | 5242855 B2 | 7/2013 | | |
| WO | 2012014978 A1 | 2/2012 | | |
| WO | WO-2012129227 A1 * | 9/2012 | ............. | C07K 16/28 |
| WO | 2015041318 A1 | 3/2015 | | |
| WO | WO-2015161218 A1 * | 10/2015 | ............... | C12N 7/00 |
| WO | 2016199904 A1 | 12/2016 | | |
| WO | WO-2016199904 A1 * | 12/2016 | ............. | A61K 38/22 |

OTHER PUBLICATIONS

Atif et al, Eur. J. Innnnunol., 2015, 45:513-524 (Year: 2015).*
Karumuthil-Meletthil et al, Diabetes, 2015, 64/4:1341-1357 abstract only (Year: 2015).*
Kobayashi et al, British J. Dermatology, 2008, 160:297-304 (Year: 2008).*
Kobiyama et al, PNAS, USA. Feb. 25, 2014, 111/8:3086-3091. (Year: 2014).*
Levitz et al, Semin Immunopathol., 2015, 37:199-207. Published online: Nov. 18, 2014 (Year: 2015).*
Moreira et al. J. Immunology. Apr. 1, 2011, 186/1 (Supp. Meeting abstracts). AAbstract No. 103.6 (Year: 2011).*
Nguyen et al Vaccine, 2013, 31:3879-3887.. Available online:Jul. 2, 2013 (Year: 2013).*
Schulke et al, PLoSONE. 9/2:e87822. 12 pages. Published: Feb. 7, 2014 (Year: 2014).*
Lemoine et al, J Allergy Clin Immunol., 2015, 136:1355-1368. Available online: Apr. 10, 2015 (Year: 2015).*
Suram et al, JBC, Mar. 3, 2006, 281/9:5506-5514. Published: Jan. 3, 2006 (Year: 2006).*

(Continued)

*Primary Examiner* — Nita M. Minnifield
(74) *Attorney, Agent, or Firm* — Suzannah K. Sundby, Esq.; Candy + Lortz LLP

(57) ABSTRACT

The present invention provides an adjuvant for vaccine including a Dectin-1 ligand and a TLR agonist, a vaccine including the adjuvant for vaccine and at least one antigen, and the like.

10 Claims, 19 Drawing Sheets

(56) References Cited

OTHER PUBLICATIONS

Suram et al, JBC, Oct. 1, 2010, 285/40:30676-30685. Published: Jul. 18, 2010 (Year: 2010).*
Fu et al, Poultry Science, 2013, 92:2866-2875. (Year: 2013).*
Takaki et al, Journal of Innate Immunity, 2018, 10:515-521. published online: Jun. 1, 2018 (Year: 2018).*
Moldoveanu et al, Vaccine, 1998, 16(11/12):1216-1224 (Year: 1998).*
Awate et al, Frontiers in Immunology, May 2013, vol. 4, Article 114, 10 pages, doi:10.3389/fimmu.2013.00114. published May 16, 2013 (Year: 2013).*
Boyaka, J. Immunology, Jul. 1, 2017:199(1):9-16..doi:10.4049/jimmunol.1601775. (Year: 2017).*
Kim et al, J. Vet. Med. Sci., 2007, 69/5:535-539 (Year: 2007).*
Lai et al, Eur Respir Rev. 2015, 24:356-360 (Year: 2015).*
Kobiyama, et al., "A Dectin-1-assisted APC-targeting TLR9-agonist as an adjuvant", Jan. 1, 2012, Publisher: Proceedings of the Japanese Society for Immunology.
Ali, et al., "Identification of immune factors regulating antitumor immunity using polymeric vaccines with multiple adjuvants", Mar. 15, 2014, pp. 1670-1681, vol. 74, No. 6, Publisher: Cancer Res.

* cited by examiner

[Figure 1]
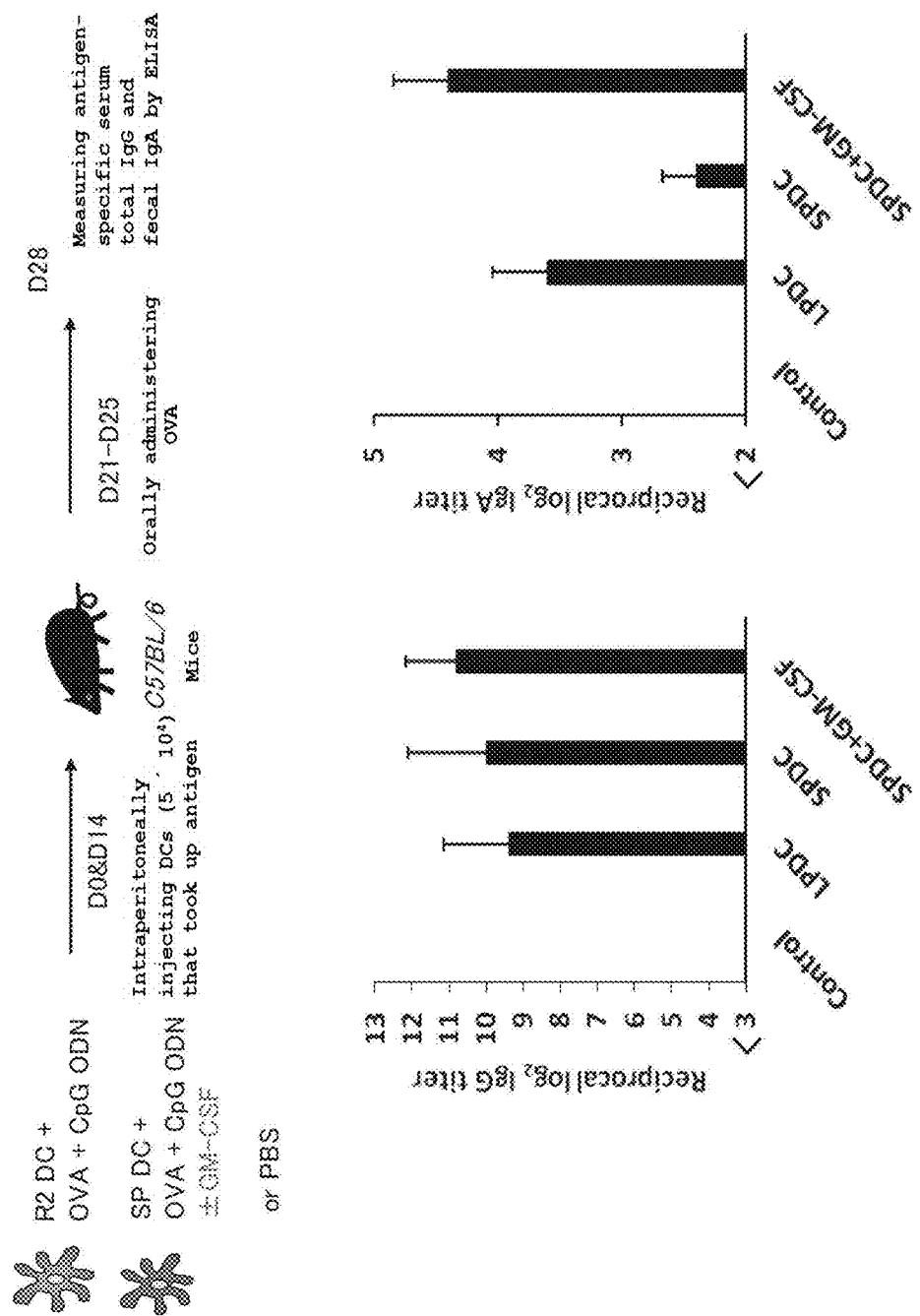

[Figure 2]
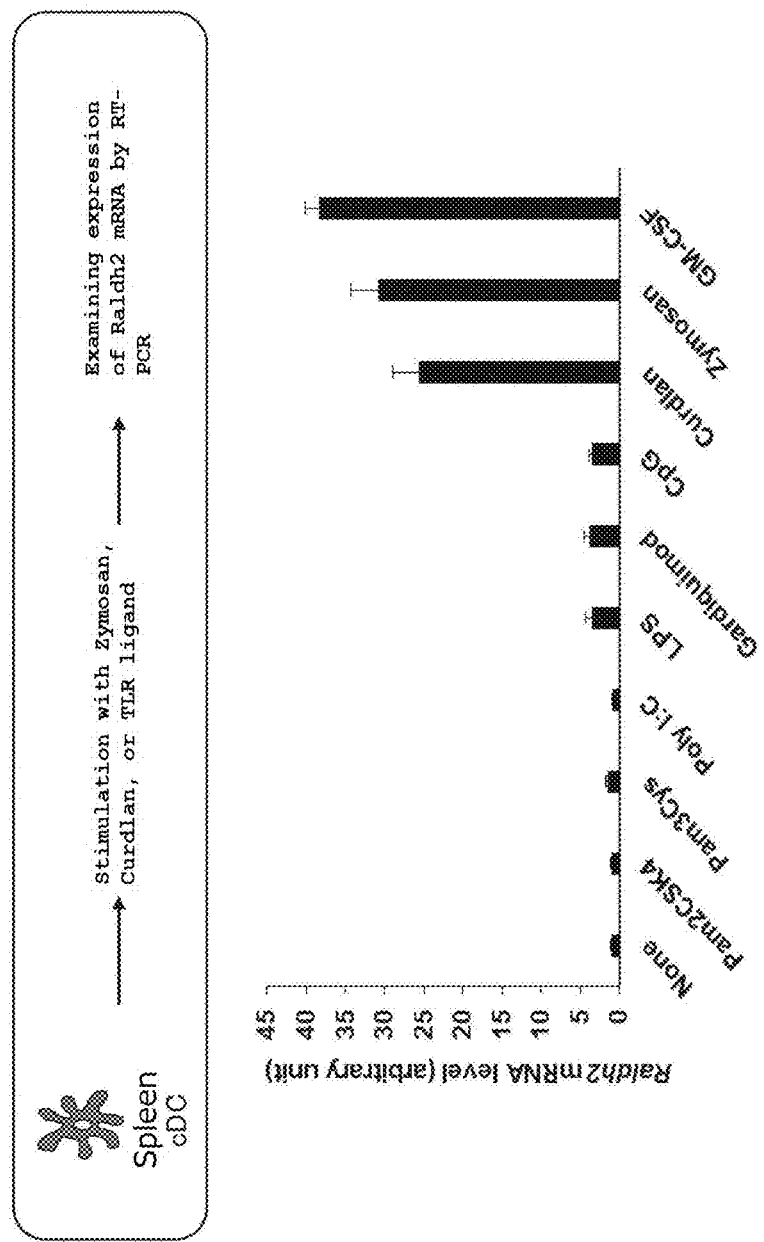

[Figure 3]
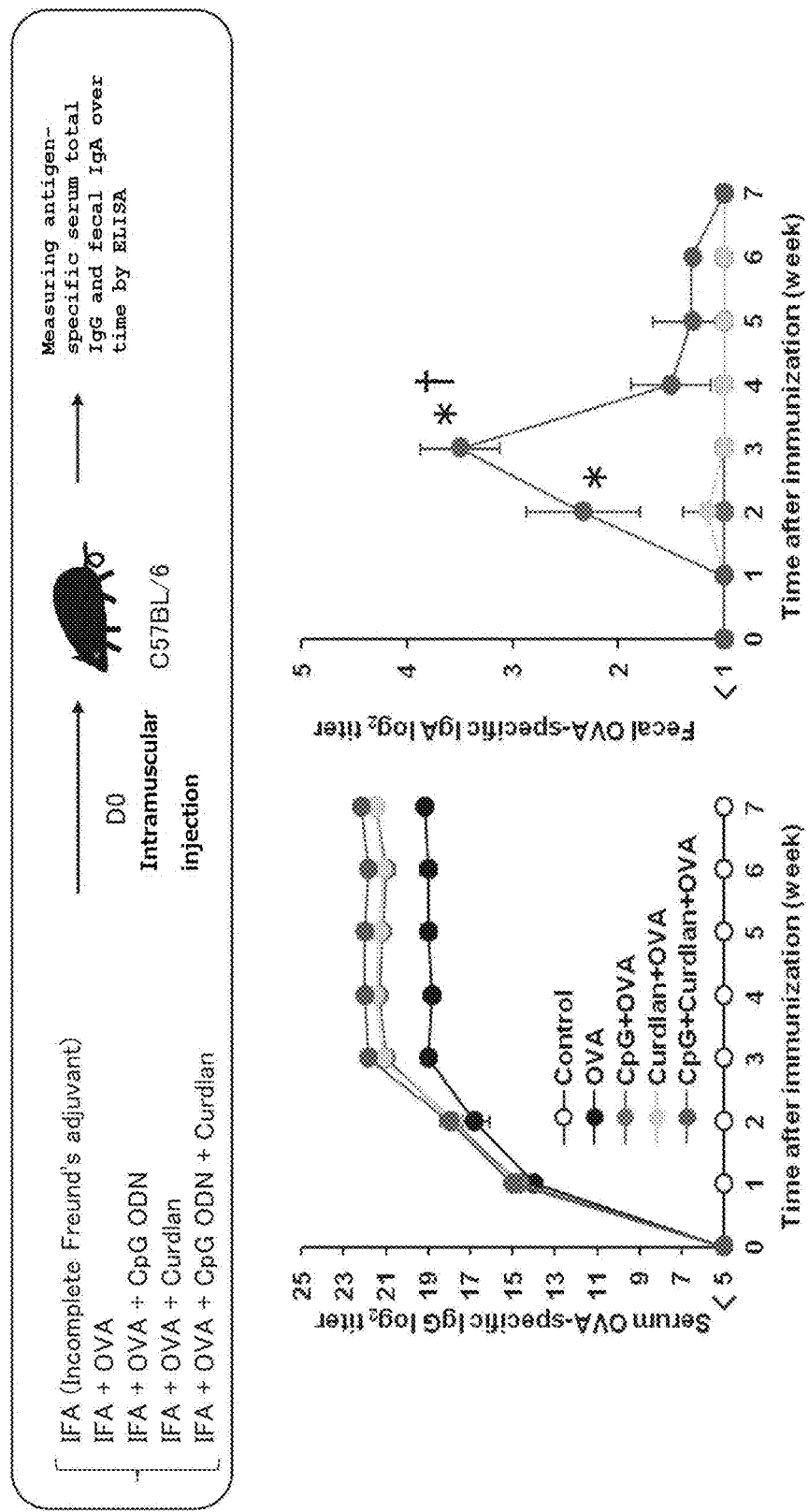

[Figure 4]
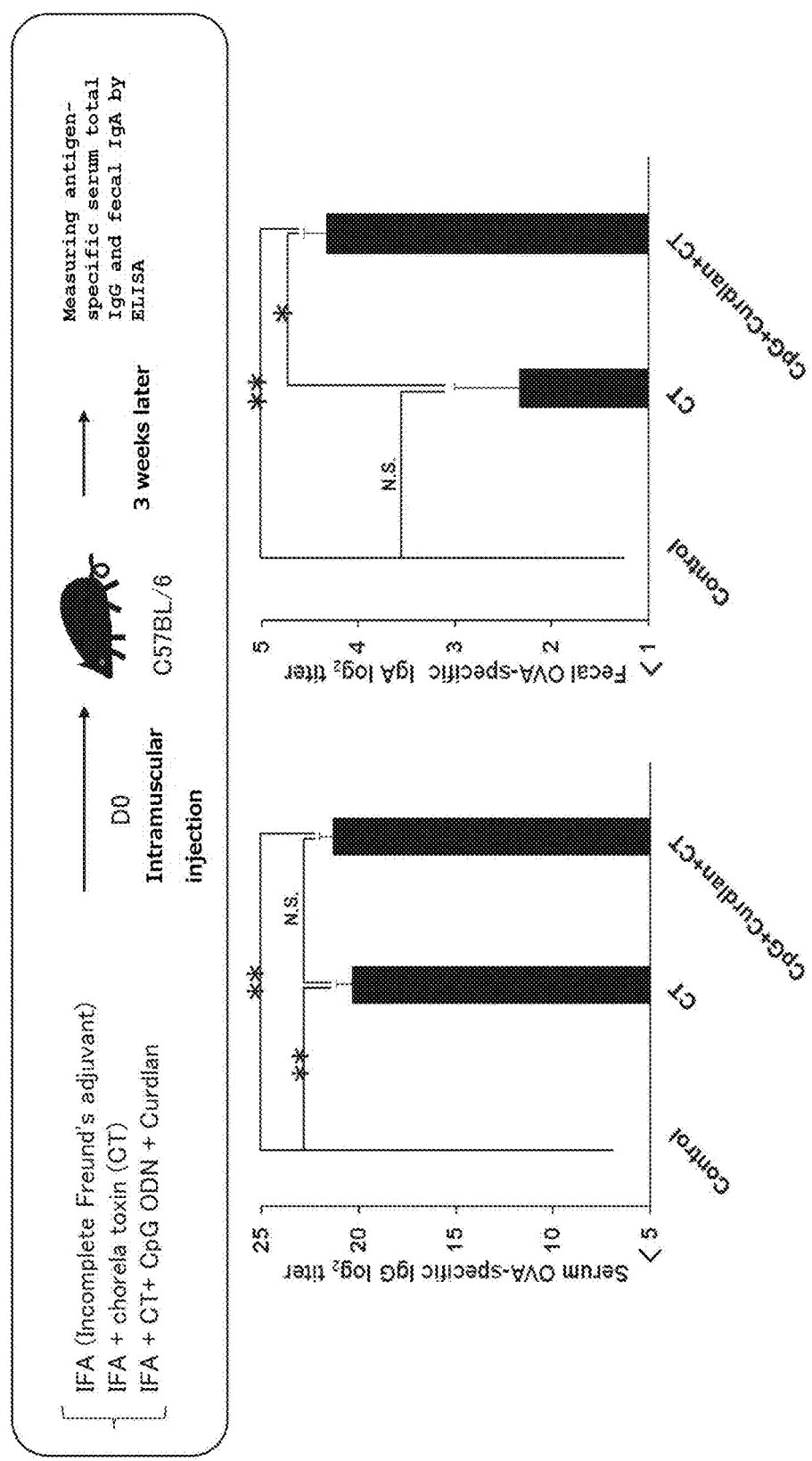

[Figure 5]
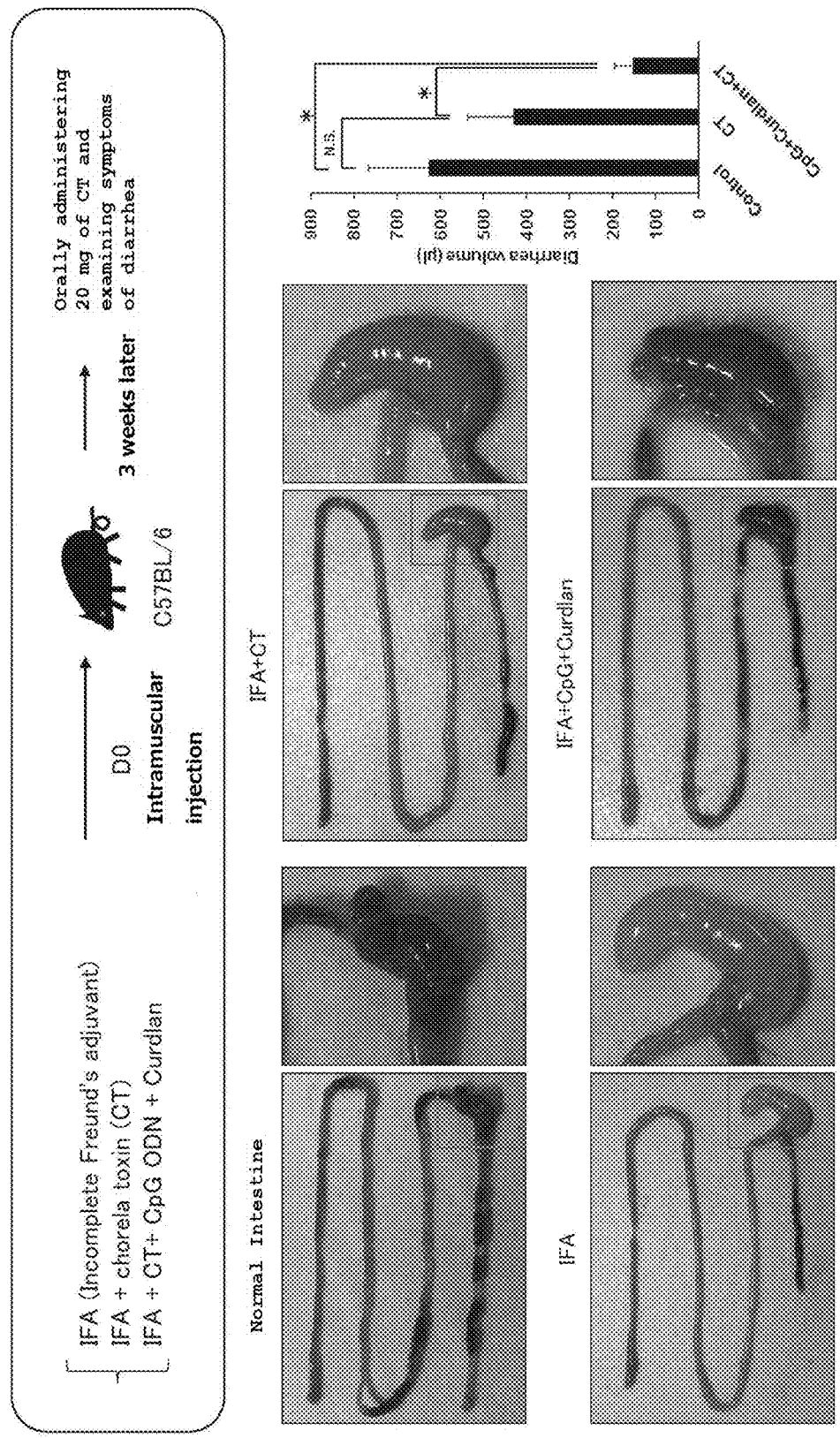

[Figure 6]
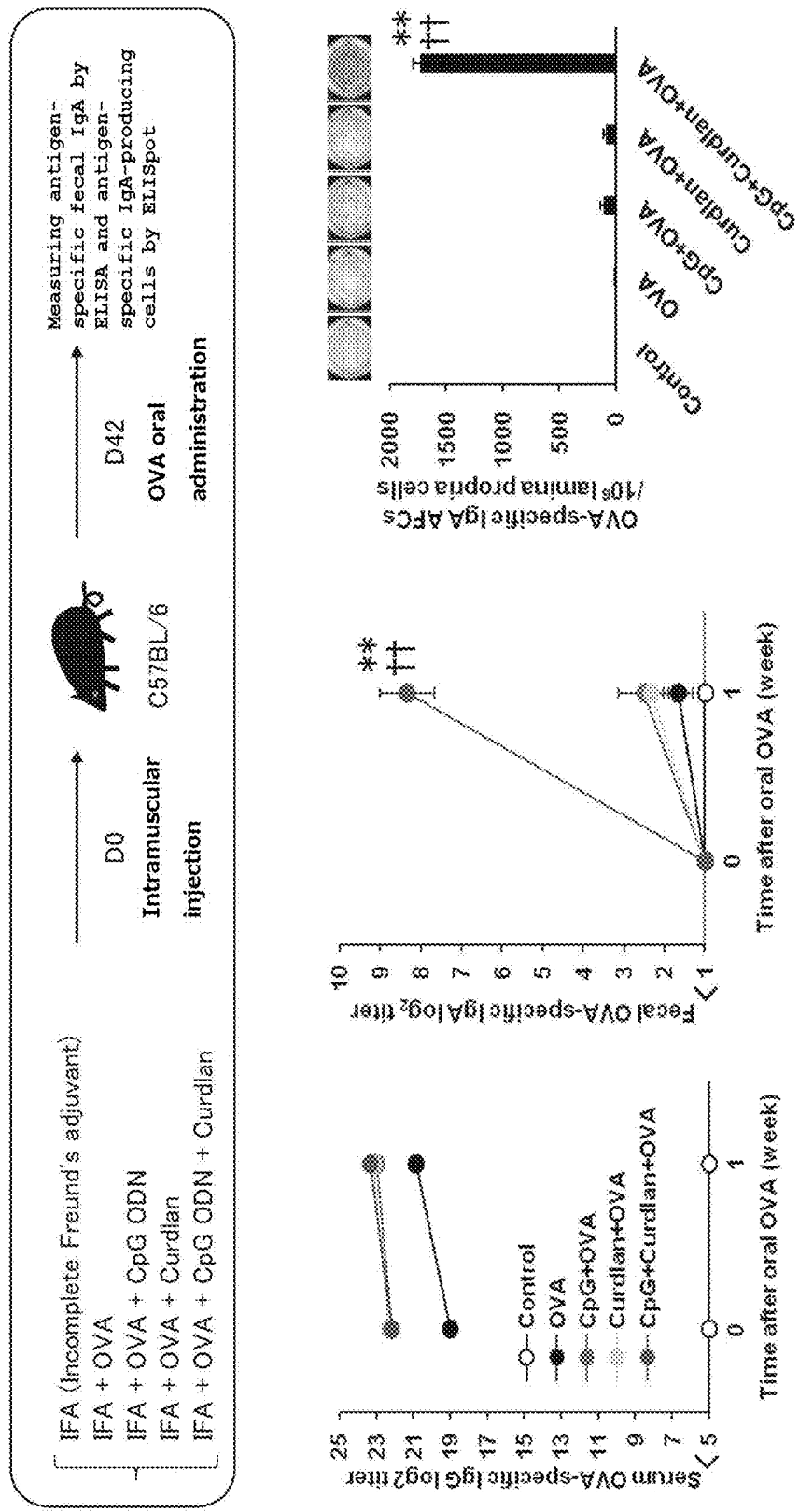

[Figure 7]
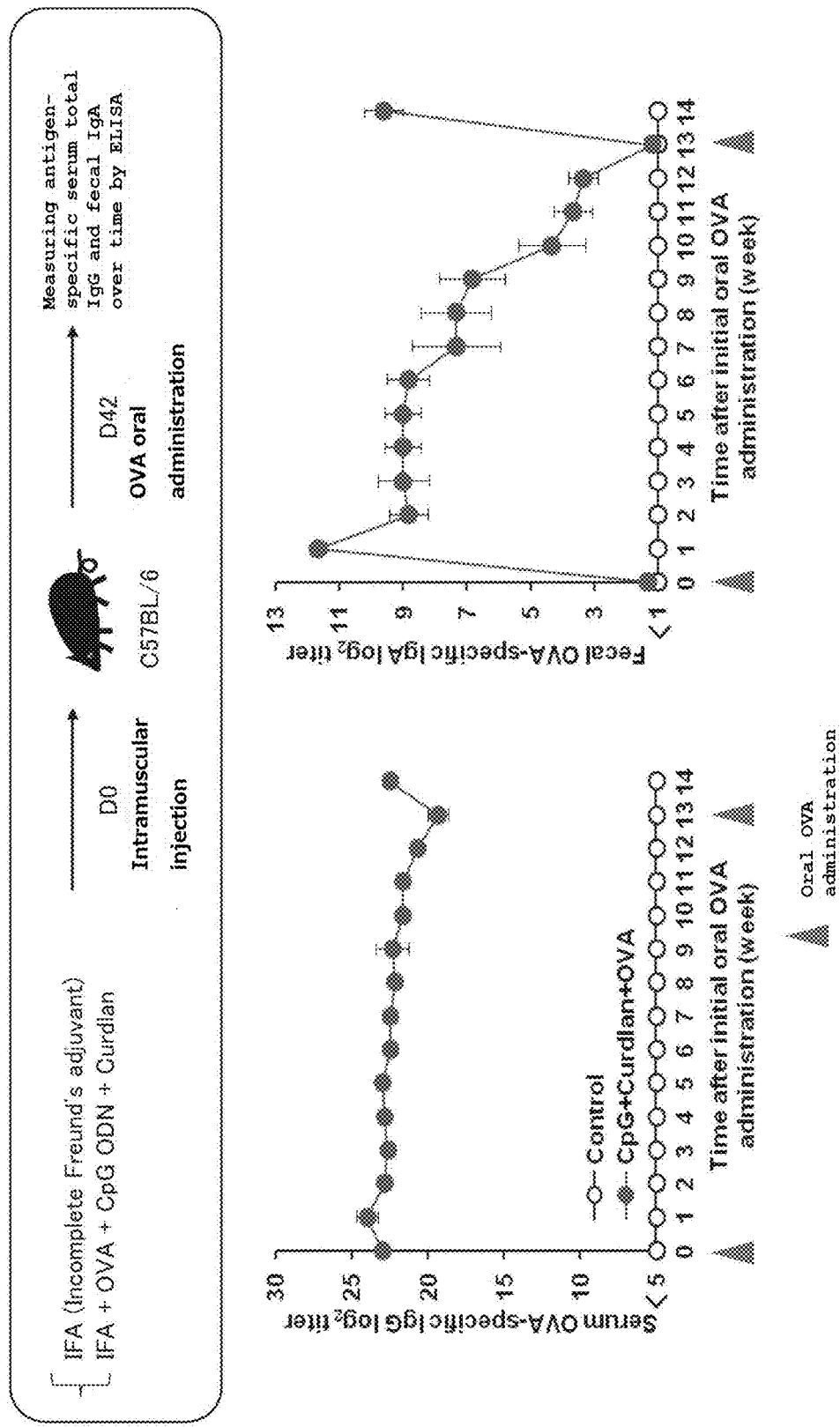

[Figure 8]
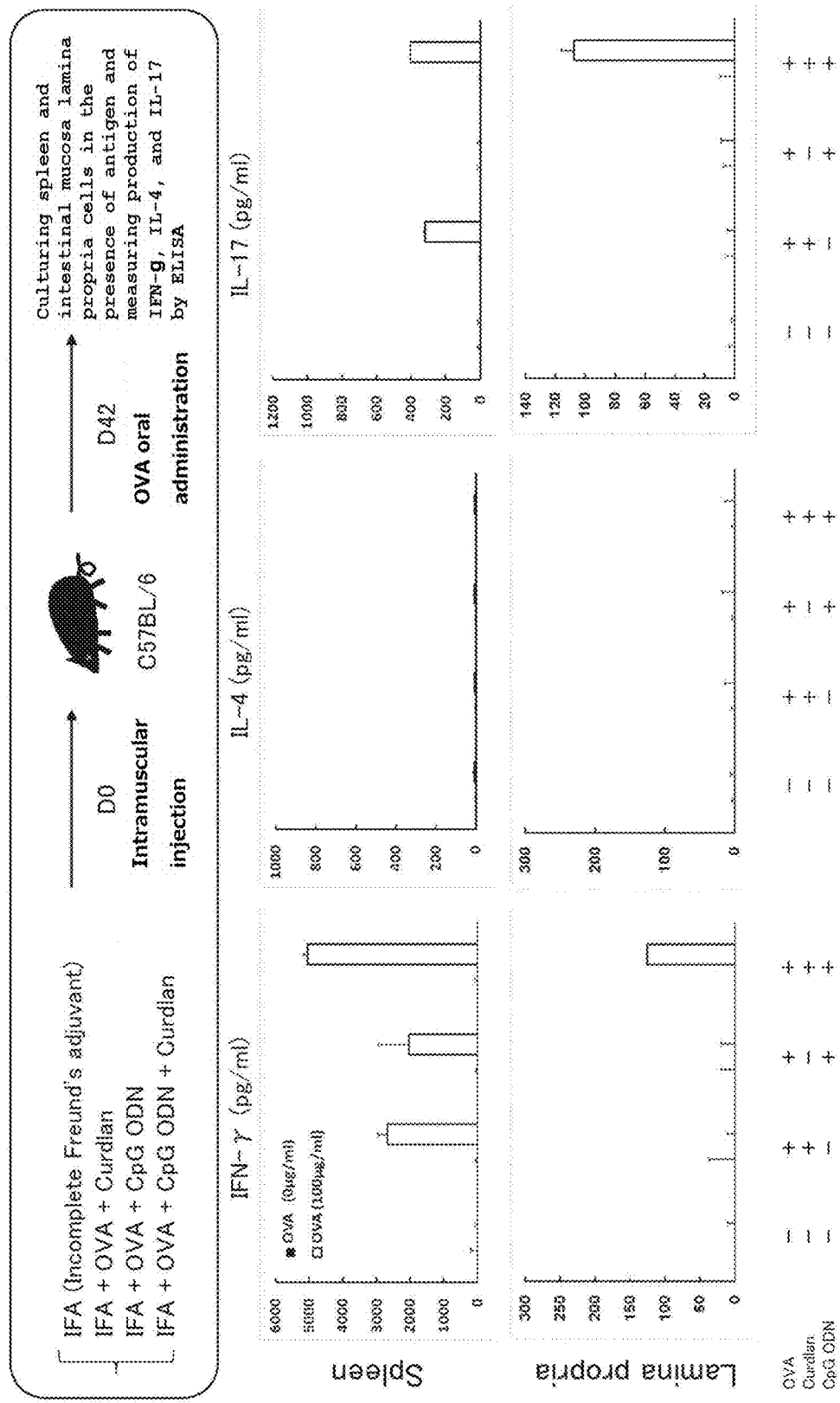

[Figure 9]
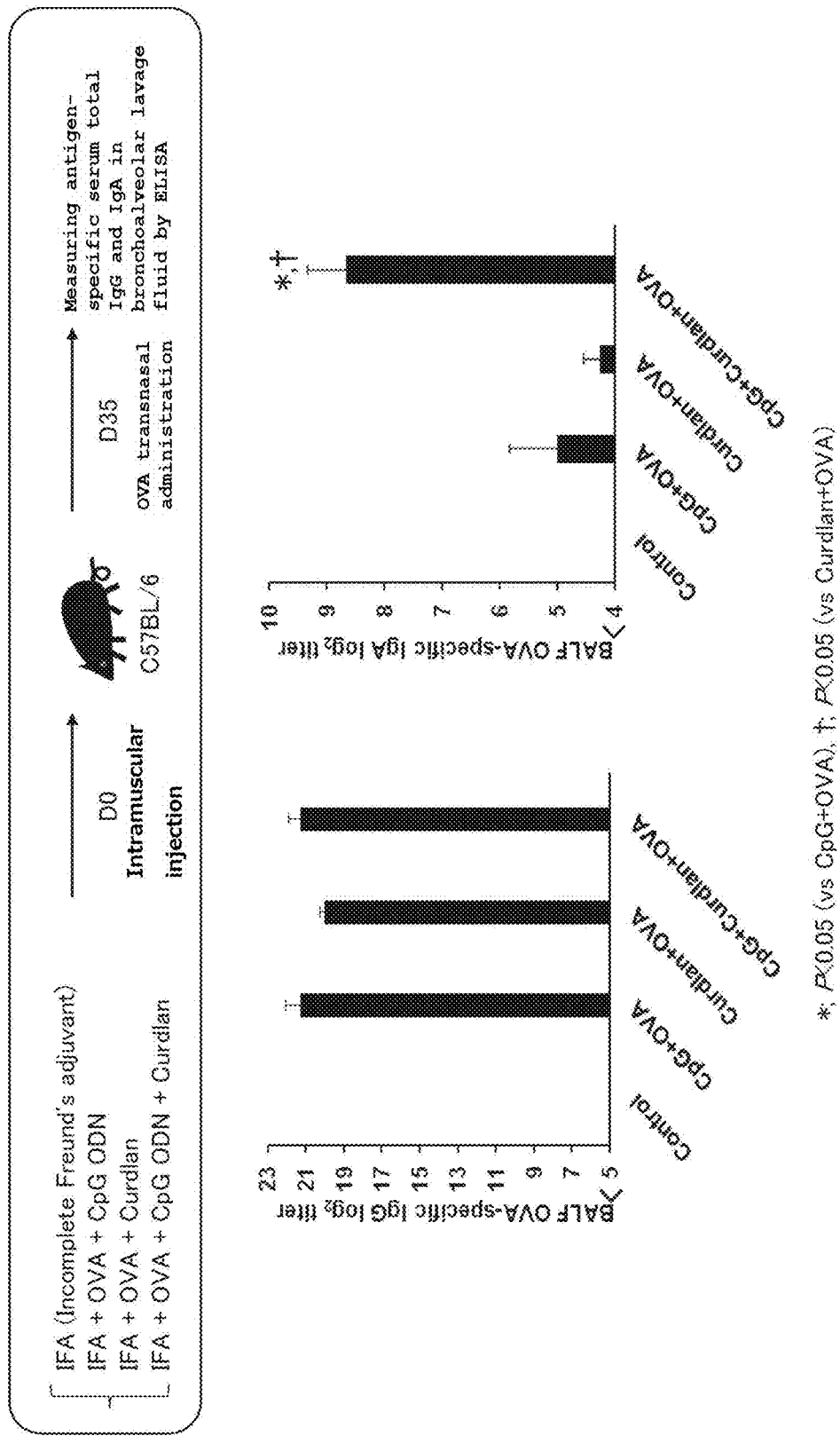

[Figure 10]
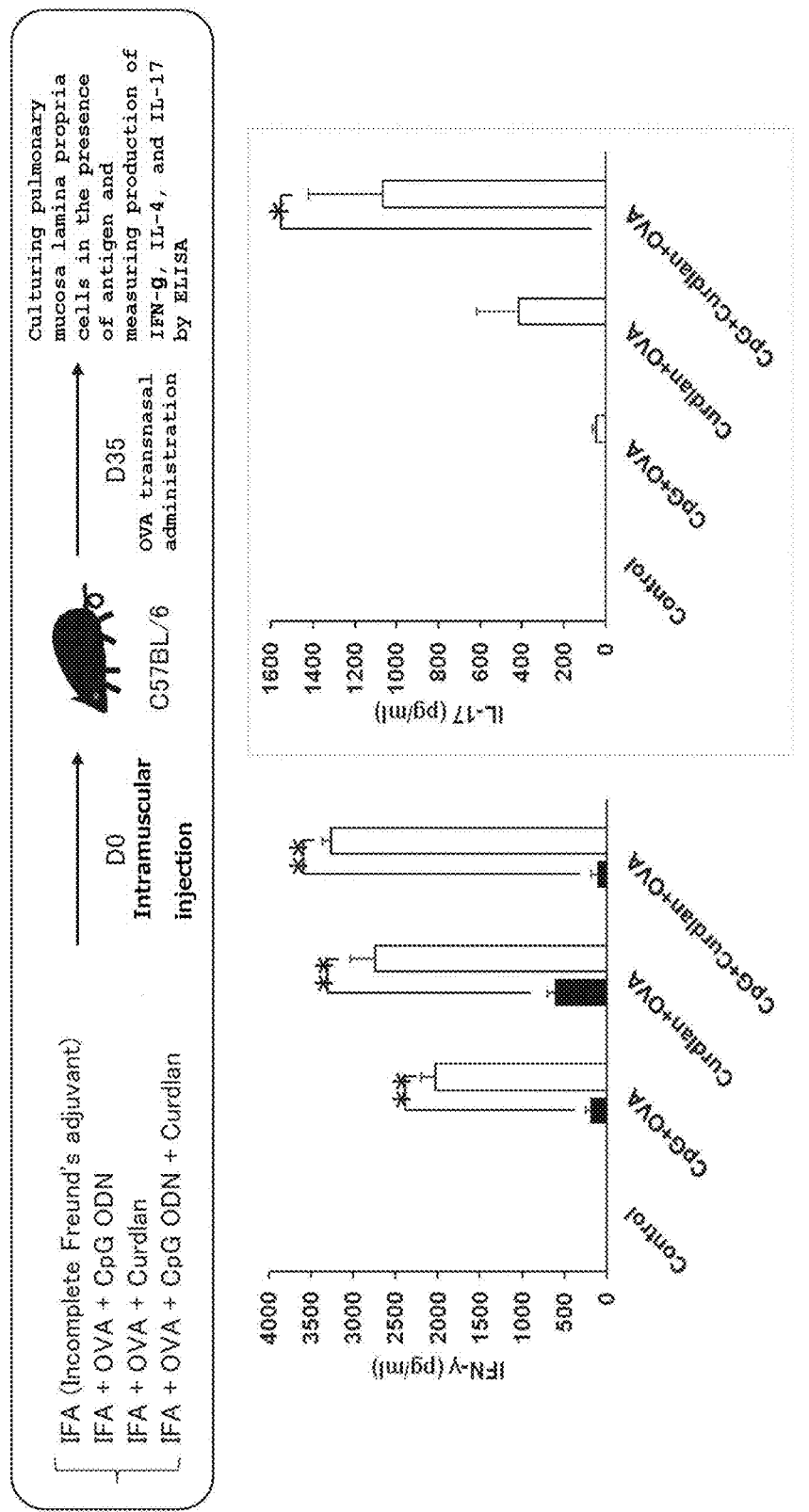

[Figure 11]
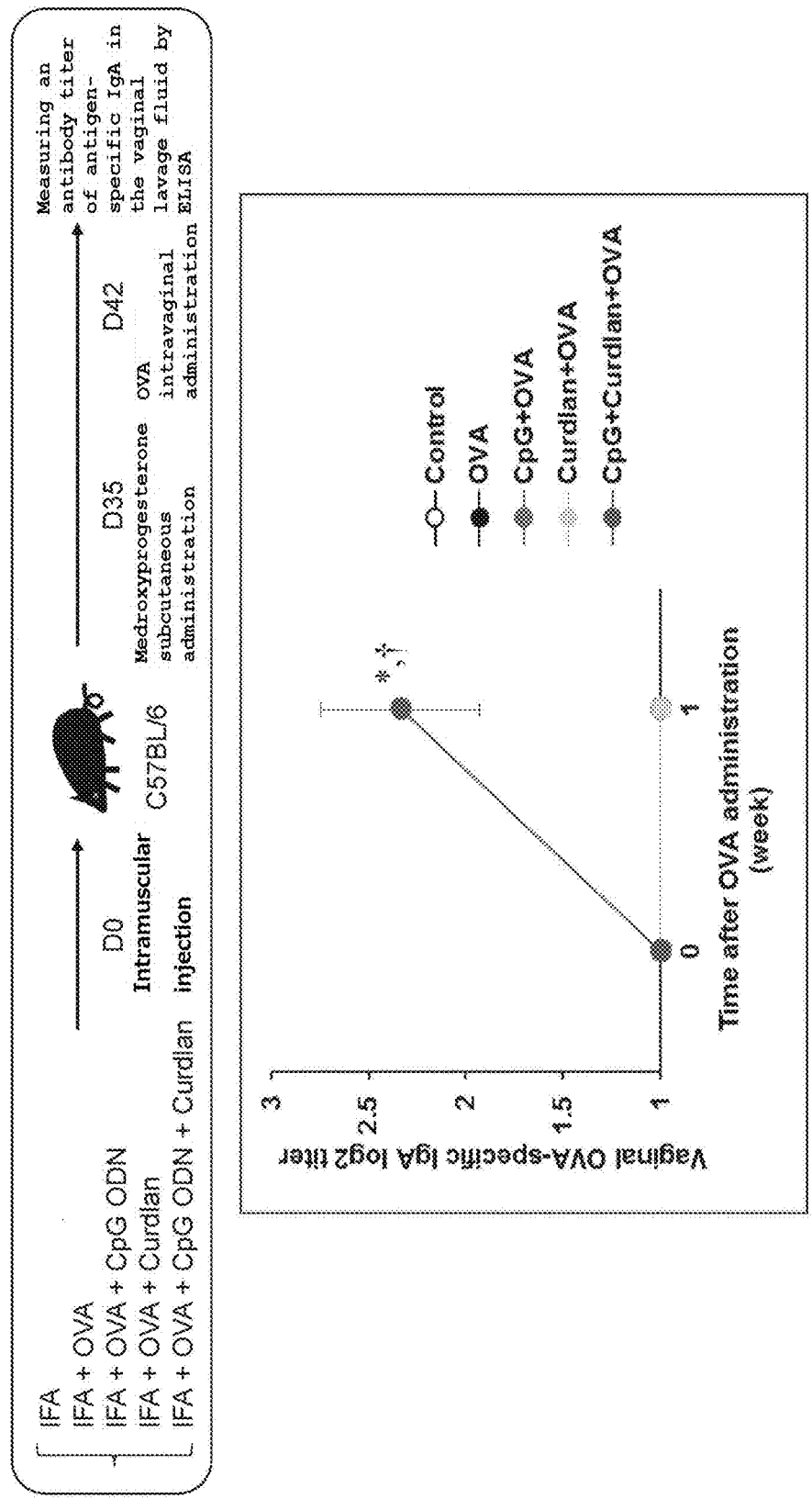

[Figure 12]
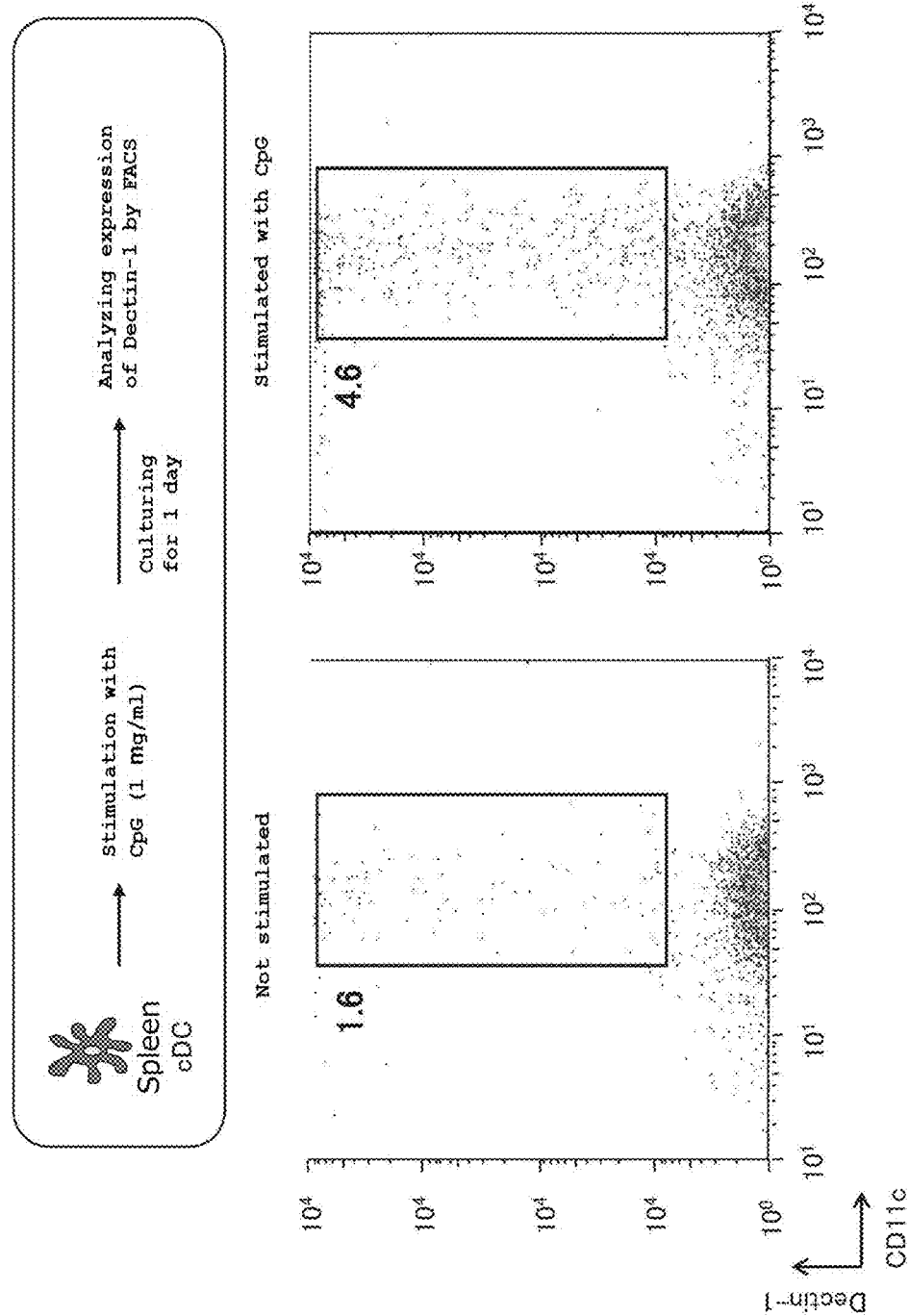

[Figure 13]
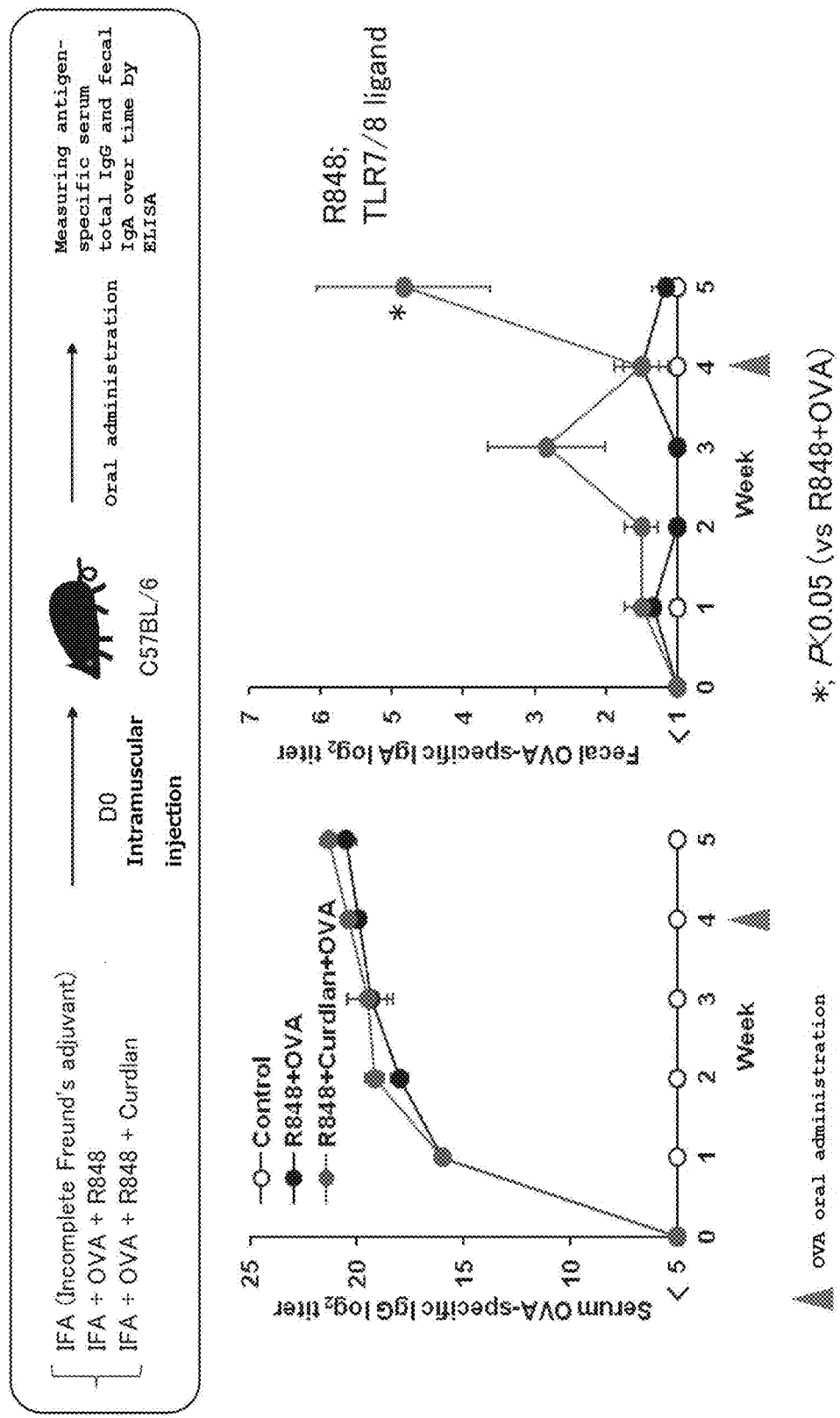

[Figure 14]
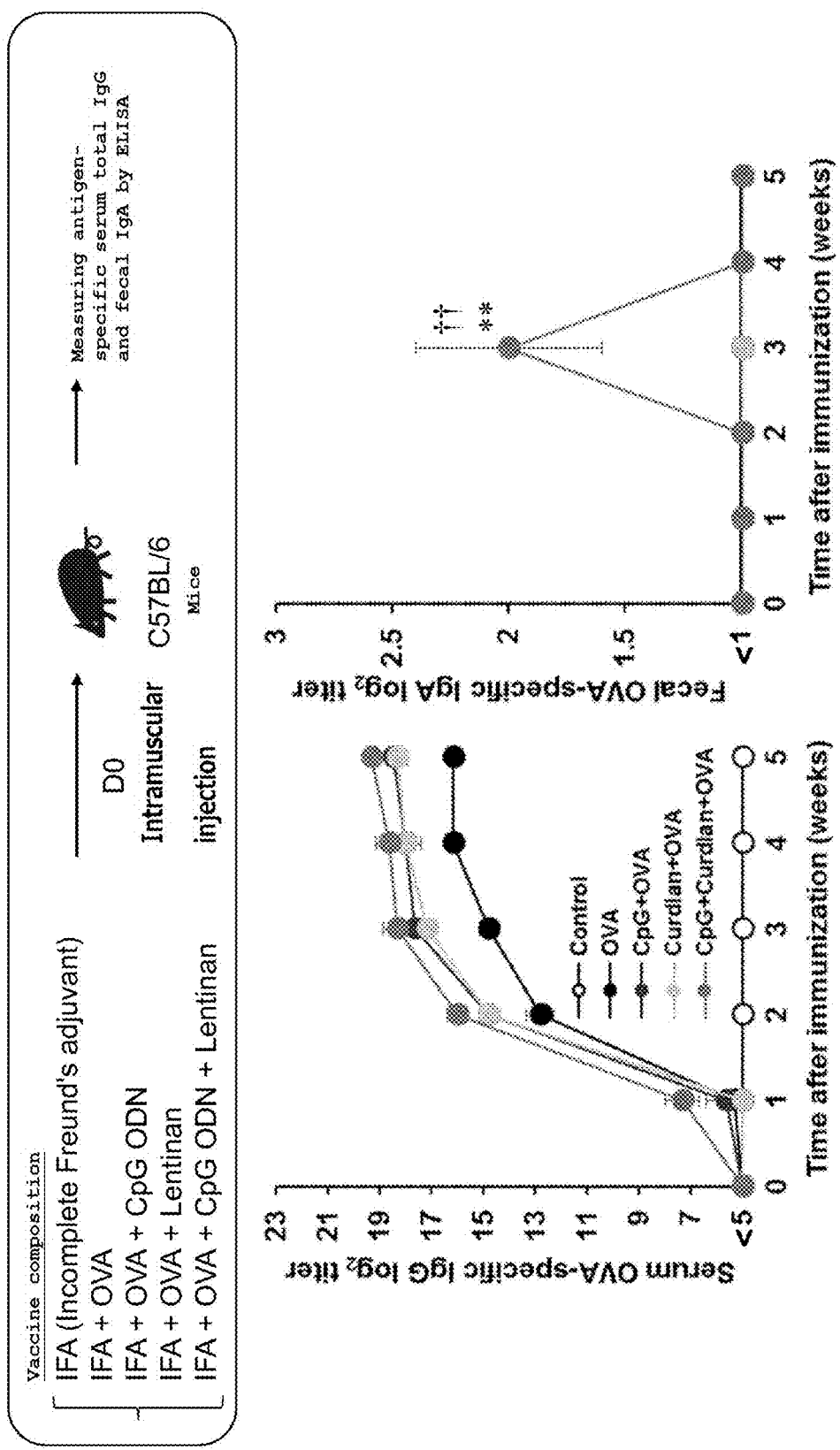

[Figure 15]
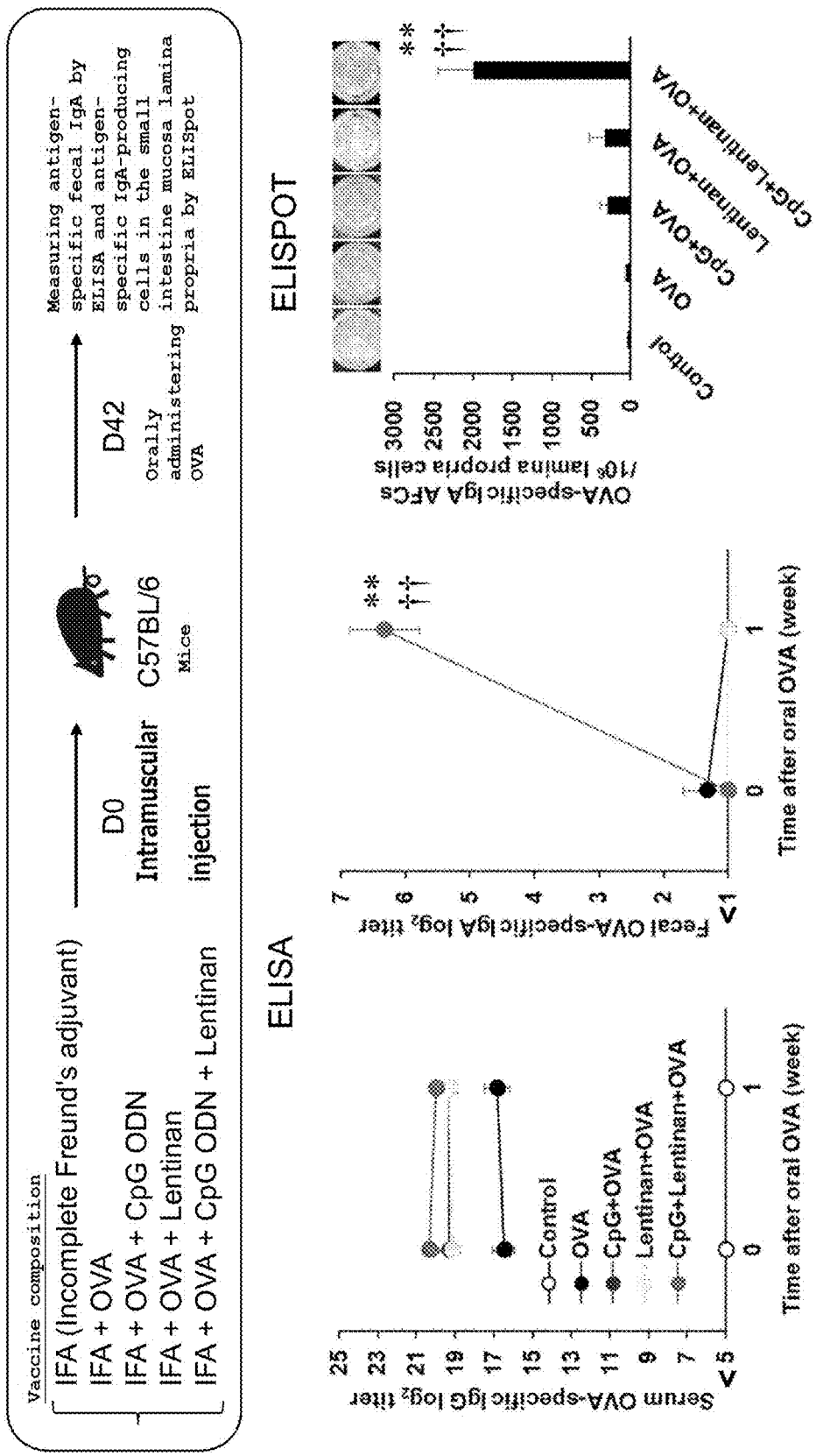

[Figure 16]
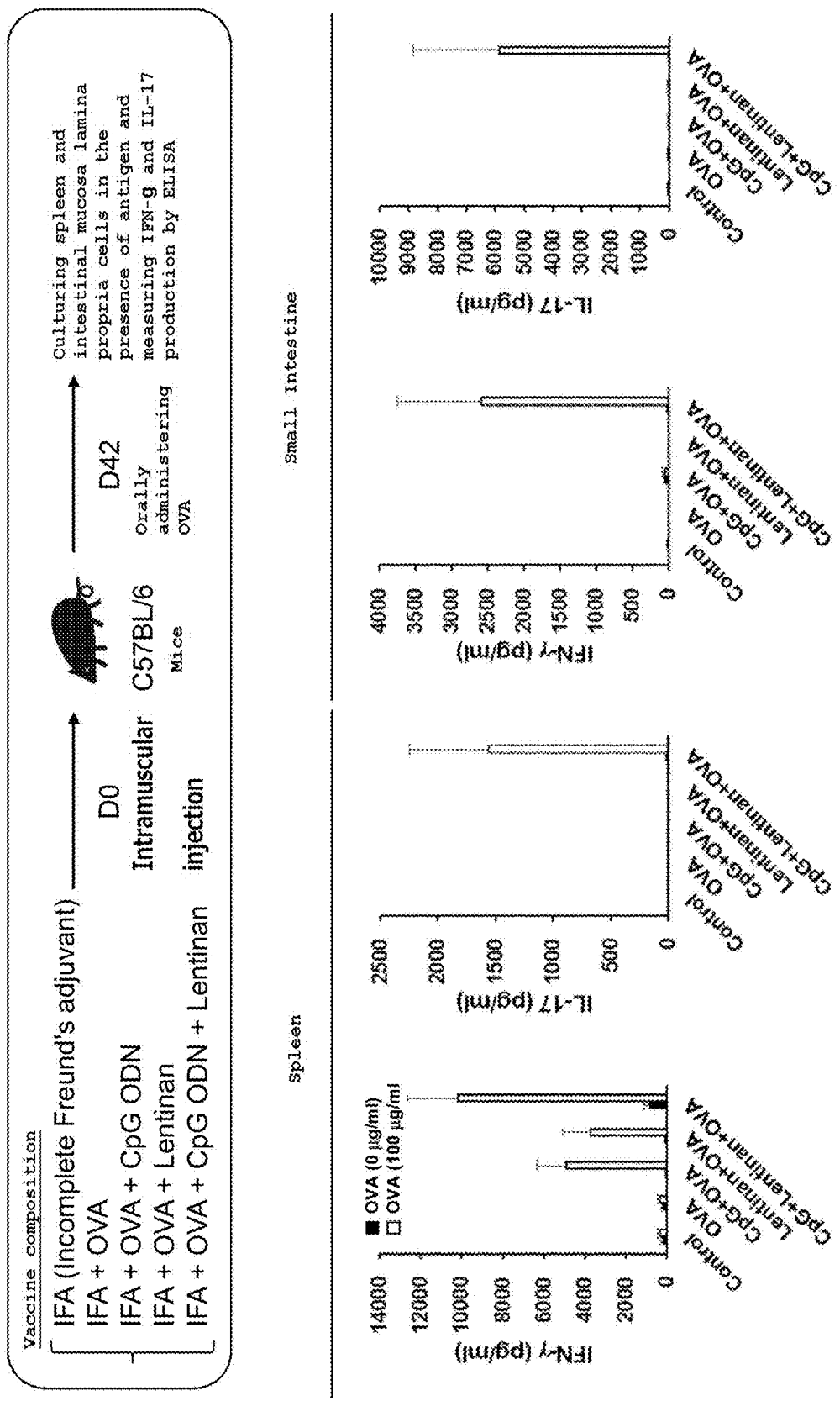

[Figure 17]
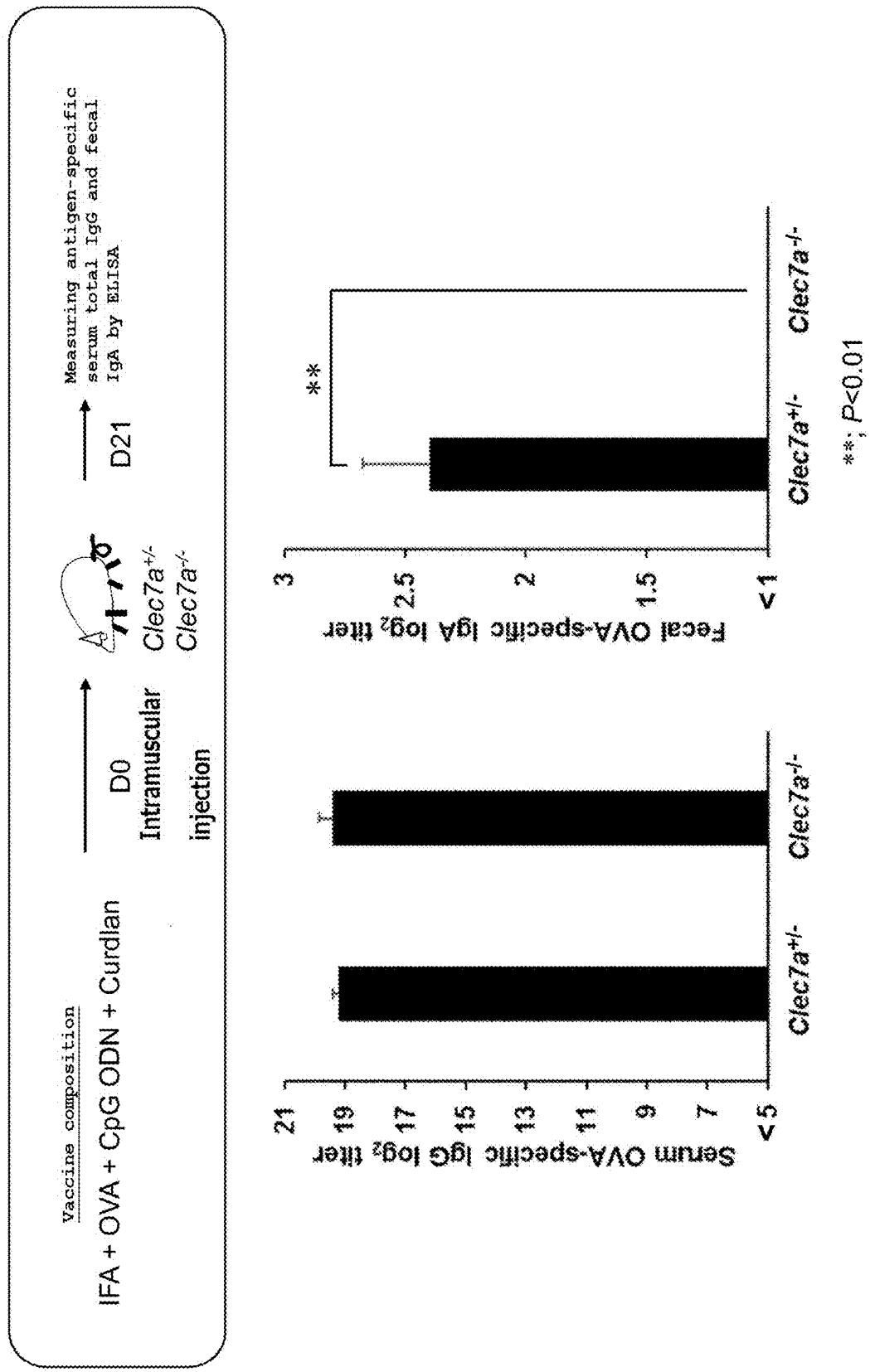

[Figure 18]
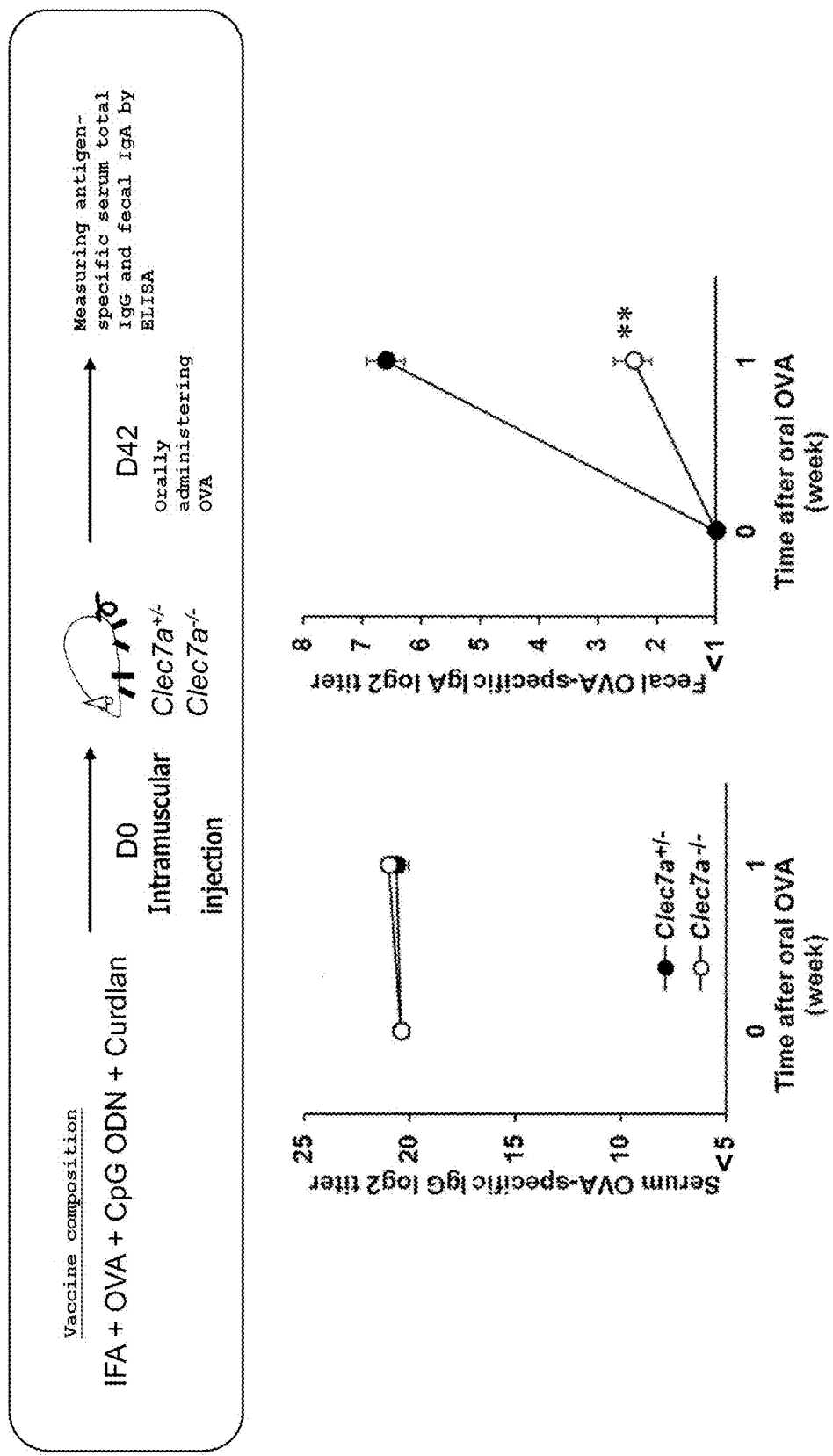

[Figure 19]
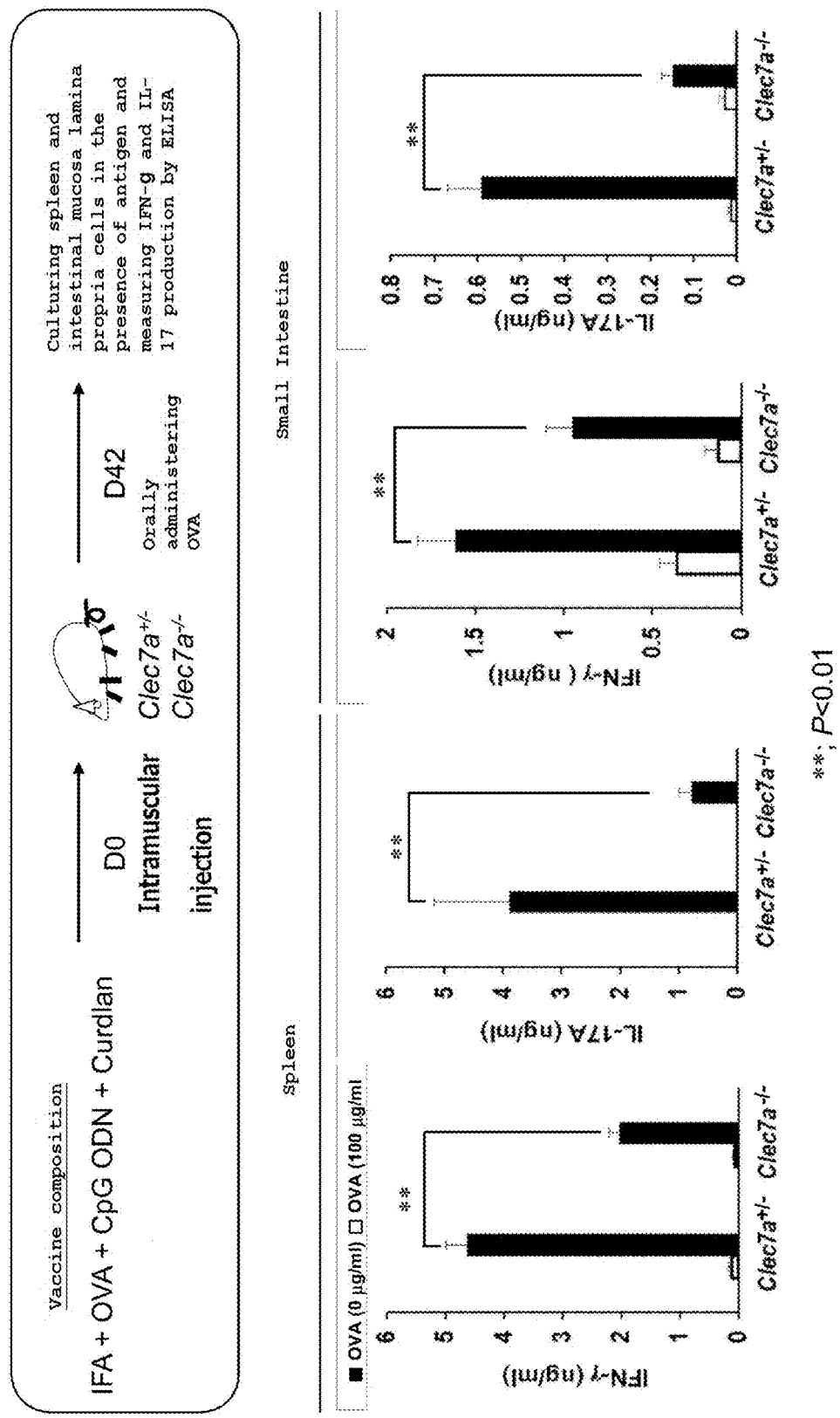

ADJUVANT FOR VACCINES, VACCINE, AND IMMUNITY INDUCTION METHOD

TECHNICAL FIELD

The present invention relates to an adjuvant for vaccine that can efficiently induce antigen-specific IgA production in the mucous membrane, a vaccine including the same, and others.

BACKGROUND ART

Many vaccines for viral and bacterial infections have been developed so far. However, most of them induce systemic immune responses that lead to IgG antibody production through the induction of a Th1 or Th2 response. Such vaccines greatly contribute to the prevention of aggravation after the infection, but cannot prevent the establishment of the infection itself. Since the entry routes of many pathogens are tissues and organs covered with the mucous membrane, such as eyes, the nasal cavity, the oral cavity, the pharynx, the respiratory tract, digestive organs, and the urogenital apparatus, it is necessary to enhance the immune response in the mucous membrane and prevent the entry for preventing the establishment of the infection itself. Therefore, there is a demand for vaccines that can induce both of the mucosal immune response represented by the IgA antibody and the systemic immune response represented by the IgG antibody.

As a way of effectively inducing both of the mucosal immune response and the systemic immune response through the mucous membrane surface, use of various adjuvants for enhancing the immune response has been studied. For example, combinations of inactivated antigens from pathogens and adjuvants containing double strand RNA and glucan-based compound have been proposed as vaccines for mucosal administration (Patent Literature 1). Moreover, it has been proposed to use a culture of a microorganism of *Aureobasidium* sp. as an immunological adjuvant for intranasal administration (Patent Literature 2). The culture of this microorganism contains β-1,3-1,6-glucan and it has also been proposed to combine the culture and Poly(I:C) in Patent Literature 2.

CITATION LIST

Patent Literature

Patent Literature 1: Japanese Patent Laid-Open No. 2009-242367
Patent Literature 2: Japanese Patent Publication No. 5242855

SUMMARY OF INVENTION

Technical Problem

However, the vaccine to be administered on the local mucous membrane of the nasal cavity or the like has low efficiency in infiltrating an antigen and it is difficult to appropriately deliver the antigen to dendritic cells that reside in the mucous membrane. Moreover, there is the problem that the effect is expected only around the administration site and the induction of systemic immune response is weak. In addition, there is the problem that the nasal immune response cannot induce the mucosal immune response on other mucous membrane tissues such as the gastrointestinal tract.

Moreover, adjuvants that can enhance the Th1 response, which is particularly effective in the defense against infection, have been used in the vaccines that have conventionally been developed. However, such an adjuvant does not confer the function to induce the mucosal immune response.

Therefore, the present inventors thought that a totally new way of immunization that can efficiently induce the mucosal immune response in addition to the systemic immune response may be developed by selecting adjuvants on the basis of conferring the function necessary for the induction of the mucosal immune response on dendritic cells and examined the possibility.

Thus, an object of the present invention is to provide an adjuvant for vaccine that can simultaneously induce antigen-specific IgA antibodies and the Th17 response as well as antigen-specific IgG antibodies and the Th1 response as a totally new way of immunization and a vaccine containing such an adjuvant.

Solution to Problem

Uematsu, S. et al., Nat Immunol., 2008 July; 9 (7): 769-76 (Non-Patent Literature 1) discloses that special dendritic cells that can induce antigen-specific IgA antibodies and the Th17 cells, unlike the dendritic cells that reside in the spleen and the bone marrow, reside in the intestinal tract. Non-Patent Literature 1 also discloses that such a special intestinal dendritic cells express Raldh2, an enzyme that catalyzes the synthesis of retinoic acid, and can synthesize retinoic acid and this ability of synthesizing retinoic acid is essential for the induction of IgA antibodies.

Moreover, Yokota A. et al. Int Immunol. 2009 April; 21 (4): 361-377 (Non-Patent Literature 2) discloses that intestinal dendritic cells are produced by entry of blood mononuclear cells into intestinal mucosa lamina propria and differentiation of the cells under the influence of GM-CSF and IL-4 in the intestine.

Thus, the present inventors found that the treatment of dendritic cells that reside in the spleen with GM-CSF, based on contents disclosed by these documents, enables the dendritic cells to express Raldh2 and induce antigen-specific IgA antibodies. Moreover, they found that glucan-based compounds such as β-1,3-glucan induces expression of Raldh2 in dendritic cells and, as a result, the dendritic cells acquire the ability to induce antigen-specific IgA antibodies.

Furthermore, they found that the administration of an antigen with an adjuvant containing a combination of β-1,3-glucan and a CpG oligodeoxynucleotide, which is a TLR9 agonist, induces antigen-specific IgG antibodies in blood and also antigen-specific IgA antibodies in feces. By this method, the induction of antigen-specific IgG antibody production lasted for a long period of time, but the IgA antibody production dissipated after a transient increase. However, the present inventors found that performing booster immunization by administering only the antigen on the mucous membrane surface induces high doses of antigen-specific IgA antibodies and the IgA production lasts 3 months or more.

Moreover, the present inventors found that although it has been reported that the β-1,3-glucan that the present inventors used activates natural immunity receptors other than Dectin-1, the target receptor on which β-1,3-glucan acts upon induction of IgA antibody production is Dectin-1 since the induction of antigen-specific IgA antibody production disappeared in Dectin-1 knockout (KO) mice to which an adjuvant containing a combination of β-1,3-glucan and a CpG oligodeoxynucleotide was administered with an antigen. This suggests that not only β-1,3-glucan, but other substances that stimulate Dectin-1 also have a similar effect.

As described above, the present inventors have found that use of a combination of a Dectin-1 ligand and a TLR agonist in dendritic cells as an adjuvant induces the systemic Th1 response and the IgG antibody production and the Th17 response in the mucous membrane and the IgA antibody production and performing booster immunization via a selected administration route re-induces the Th17 response and the IgA antibody production in a desired mucous membrane, such as those of the intestinal tract and the respiratory tract, thereby completing the present invention.

Accordingly, the present invention provides the following.

[1]
An adjuvant for vaccine comprising
a Dectin-1 ligand and
a TLR agonist.

[2]
The adjuvant for vaccine according to [1], wherein the Dectin-1 ligand is an inducer of expression of a Raldh2 gene.

[3]
The adjuvant for vaccine according to [2], wherein the inducer of expression of a Raldh2 gene is granulocyte monocyte colony stimulating factor (GM-CSF) or a glucan-based compound.

[4]
The adjuvant for vaccine according to any of [1] to [3], further comprising an incomplete Freund's adjuvant.

[5]
The adjuvant for vaccine according to any of [1] to [4], for administration with at least one antigen.

[6]
A vaccine comprising
at least one antigen and
an adjuvant for vaccine according to any of [1] to [5].

[7]
The vaccine according to [6], wherein the vaccine is a vaccine composition comprising the antigen and the adjuvant for vaccine.

[8]
The vaccine according to [6] or [7], wherein the at least one antigen is an inactivated or attenuated virus or a part thereof or a component thereof; an inactivated or attenuated bacterium or a part thereof or a component thereof; or an allergen.

[9]
The vaccine according to any of [6] to [8], wherein the vaccine induces antigen-specific IgA production.

[10]
The vaccine according to any of [6] to [9], wherein the vaccine induces antigen-specific IgA production and antigen-specific IgG production.

[11]
The vaccine according to any of [6] to [10], wherein the vaccine induces a mucosal immune response.

[12]
The vaccine according to any of [6] to [11], wherein the vaccine is administered by administering the vaccine in a mode selected from the group consisting of transdermal administration, subcutaneous administration, intradermal administration, and intramuscular administration.

[13]
The vaccine according to any of [6] to [12], wherein the vaccine is used in a method for inducing immunity, comprising administering the vaccine, and then performing at least once of booster immunization involving administering an antigen a certain period of time after the vaccine administration.

[14]
The vaccine according to [13], wherein the booster immunization is performed by administering an antigen in a mode selected from the group consisting of oral administration, intranasal administration, transmucosal administration, transvaginal administration, ophthalmic administration, and intrarectal administration.

[15]
The vaccine according to [13] or [14], wherein the booster immunization is performed by administering an antigen without using any adjuvant.

[16]
A method for inducing immunity, comprising
a step of administering a vaccine comprising
at least one antigen and
an adjuvant for vaccine comprising a Dectin-1 ligand and a TLR agonist.

[17]
The method for inducing immunity according to [16], wherein the step of administering a vaccine is performed by administering the vaccine in a mode selected from the group consisting of transdermal administration, subcutaneous administration, intradermal administration and intramuscular administration.

[18]
The method for inducing immunity according to [16] or [17], further comprising
a step of administering an antigen a certain period of time after the step of administering a vaccine to perform booster immunization.

[19]
The method for inducing immunity according to [18], wherein the step of performing booster immunization is performed by administering an antigen in a mode selected from the group consisting of oral administration, intranasal administration, transmucosal administration, transvaginal administration, ophthalmic administration, and intrarectal administration.

[20]
The method for inducing immunity according to [18] or [19], wherein the step of performing booster immunization is performed by administering an antigen without using any adjuvant.

[21]
A method for preventing a virus infection, a bacterial infection, or allergy, comprising
a step of administering a vaccine comprising
at least one antigen derived from virus, bacterium, or allergen and
an adjuvant for vaccine comprising a Dectin-1 ligand and a TLR agonist.

Advantageous Effects of Invention

According to the present invention, the suppression of both of the entry of pathogens and aggravation of the disease condition can be achieved since both of the systemic immune response represented by the Th1 response and antigen-specific IgG antibody production and the mucosal immune response represented by the Th17 response and antigen-specific IgA antibody production can effectively be induced to a desired antigen by a simple method involving use of a combination of a Dectin-1 ligand and a TLR agonist as an adjuvant.

Moreover, although the induction of the mucosal immune response disappears in a relatively short period of time, while the induction of the systemic immune response lasts for a long period of time, when the immune response is induced with such an adjuvant, further booster immunization involving administering only the antigen on the mucous membrane surface can make the induction of the mucosal immune response last for a long period of time. It is also possible to induce the mucosal immune response at the desired site, such as the intestinal tract and the respiratory tract, by selecting the administration route of the antigen as appropriate upon the booster immunization.

BRIEF DESCRIPTION OF DRAWINGS

FIG. 1 illustrates the result of intraperitoneally administering spleen-derived dendritic cells stimulated with an antigen (OVA), CpG ODN, and GM-CSF to mice, then orally administering the antigen, and measuring total of antigen-specific IgG in serum and antigen-specific IgA in feces.

FIG. 2 illustrates the result of stimulating spleen-derived dendritic cells with glucan-based compound (zymosan or curdlan) or various TLR agonists and measuring expression of Raldh2.

FIG. 3 illustrates the result of administering an IFA emulsion containing an antigen (OVA) and an adjuvant (CpG ODN and/or curdlan) to mice by intramuscular injection and measuring total of antigen-specific IpG in serum and antigen-specific IgA in feces over time.

FIG. 4 illustrates the result of administering an IFA emulsion containing an antigen (cholera toxin) and an adjuvant (CpG ODN and curdlan) to mice by intramuscular injection and measuring antigen-specific serum total IgG and fecal IgA 3 weeks later.

FIG. 5 illustrates the result of orally administering the cholera toxin to the mice after the experiment of FIG. 4 and examining symptoms of the diarrhea.

FIG. 6 illustrates the result of administering an IFA emulsion containing an antigen (OVA) and an adjuvant (CpG ODN and/or curdlan) to mice by intramuscular injection, performing booster immunization with the antigen 42 days later, and measuring total of antigen-specific IpG in serum and antigen-specific IgA in feces on the day and 1 week later.

FIG. 7 illustrates the result of administering an IFA emulsion containing an antigen (OVA) and an adjuvant (CpG ODN and/or curdlan) to mice by intramuscular injection, performing booster immunization with the antigen 42 days later, and then measuring total of antigen-specific IpG in serum and antigen-specific IgA in feces over time. After the first booster immunization, the second booster immunization was performed in the thirteenth week.

FIG. 8 illustrates the result of administering an IFA emulsion containing an antigen (OVA) and an adjuvant (CpG ODN and/or curdlan) to mice by intramuscular injection, performing booster immunization 42 days later, extracting cells in the spleen and intestinal mucosa lamina propria from the mice 7 days later and culturing the cells in the presence of the antigen, and measuring the production of IFN-γ, IL-4, and IL-17 4 days later.

FIG. 9 illustrates the result of administering an IFA emulsion containing an antigen (OVA) and an adjuvant (CpG ODN and/or curdlan) to mice by intramuscular injection, administering the antigen by intranasal administration 35 days later to perform booster immunization, and measuring total of antigen-specific IpG in serum and antigen-specific IgA in the bronchoalveolar lavage fluid 7 days later.

FIG. 10 illustrates the result of administering an IFA emulsion containing an antigen (OVA) and an adjuvant (CpG ODN and/or curdlan) to mice by intramuscular injection, administering the antigen by intranasal administration 35 days later to perform booster immunization, extracting pulmonary mucosa lamina propria cells from the mice 7 days later and culturing the cells in the presence of the antigen, and measuring IFN-γ and IL-17 production by ELISA 4 days later.

FIG. 11 illustrates the result of administering an IFA emulsion containing an antigen (OVA) and an adjuvant (CpG ODN and/or curdlan) to mice by intramuscular injection, administering Medroxyprogesterone 35 days later, intravaginally administering the antigen 42 days later to perform booster immunization, and measuring antigen-specific IgA in the vaginal lavage fluid 7 days later.

FIG. 12 illustrates the result of measuring the expression of dectin-1, a receptor of β-1,3-glucan, in spleen-derived dendritic cells with or without stimulation of CpG ODN.

FIG. 13 illustrates the result of administering an IFA emulsion containing an antigen (OVA) and an adjuvant (R-848 only or R-848 and curdlan) to mice by intramuscular injection, orally administering the antigen on the 28th day to perform booster immunization, and then measuring total of antigen-specific IpG in serum and antigen-specific IgA in feces over time. The second booster immunization was performed 4 weeks after the first booster immunization.

FIG. 14 illustrates the result of administering an IFA emulsion containing an antigen (OVA) and an adjuvant (CpG ODN and/or lentinan) to mice by intramuscular injection and measuring total of antigen-specific IpG in serum and antigen-specific IgA in feces over time.

FIG. 15 illustrates the result of administering an IFA emulsion containing an antigen (OVA) and an adjuvant (CpG ODN and/or lentinan) to mice by intramuscular injection, performing booster immunization with the antigen 42 days later, and measuring total of antigen-specific IpG in serum and antigen-specific IgA in feces on the day and 1 week later.

FIG. 16 illustrates the result of administering an IFA emulsion containing an antigen (OVA) and an adjuvant (CpG ODN and/or lentinan) to mice by intramuscular injection, performing booster immunization 42 days later, extracting cells in the spleen and intestinal mucosa lamina propria from the mice 7 days later and culturing the cells in the presence of the antigen, and measuring the production of IFN-γ and IL-17 4 days later.

FIG. 17 illustrates the result of administering an IFA emulsion containing an antigen (OVA) and an adjuvant (CpG ODN and curdlan) to Dectin-1 deficient mice by intramuscular injection and measuring total of antigen-specific IpG in serum and antigen-specific IgA in feces 21 days later.

FIG. 18 illustrates the result of administering an IFA emulsion containing an antigen (OVA) and an adjuvant (CpG ODN and lentinan) to Dectin-1 deficient mice by intramuscular injection, performing booster immunization with the antigen 42 days later, and measuring total of antigen-specific IpG in serum and antigen-specific IgA in feces on the day and 1 week later.

FIG. 19 illustrates the result of administering an IFA emulsion containing an antigen (OVA) and an adjuvant (CpG ODN and curdlan) to Dectin-1 deficient mice by intramuscular injection, performing booster immunization 42 days later, extracting cells in the spleen and intestinal mucosa lamina propria from the mice 7 days later and culturing the cells in the presence of the antigen, and measuring the production of IFN-γ and IL-17 4 days later.

DESCRIPTION OF EMBODIMENTS (Adjuvant for Vaccine)

An adjuvant for vaccine according to the present invention comprises a Dectin-1 ligand and a TLR agonist.

As used herein, the term "vaccine" refers to a pharmaceutical preparation used for the purpose of the prevention of infection and contains a deactivated or attenuated antigen. The vaccine can induce the immune response when administered to an animal such as a human and prevent the infection (including allergic reactions) with the antigen contained in the vaccine and the aggravation of the infection after the induction. The reasons why the adjuvant for vaccine according to the present invention has the effect according to the present invention and the like will be explained below mainly through effects of vaccines (or adjuvants for vaccine) of the conventional art or physiological functions of animals.

First, while vaccines to be administered on the mucous membrane, such as intranasal or oral vaccines, induce the mucosal immune response and the systemic immune response, the conventional vaccines to be intramuscularly administered induce only the systemic immune response, but not the mucosal immune response. Here, dendritic cells reside widely in tissues and, upon the recognition of an antigen that has entered the body, move to neighboring lymph nodes and induce and spread throughout the body the antigen-specific response including the production of antibodies. The dendritic cells in the mucosal tissues or the lymph nodes associated therewith also have the function for inducing IgA antibody production unlike the dendritic cells in non-mucosal tissues. The IgA antibody-producing cells induced are under the influence of such dendritic cells and promoted to transfer to an associated mucosa tissue to provide strong defense locally. It is inferred that such difference between the properties of the dendritic cells has a great influence on the difference between the effects of the mucosal administration of a vaccine and of the administration of the vaccine by intramuscular injection. Therefore, conventional vaccines cannot induce the mucosal immune response when administered intramuscularly since no dendritic cells that can induce IgA reside there and the mucosal immune response is induced only when the immunization is given through the mucous membrane surface. In general, the immunization needs to be given via the respiratory tract mucosa when IgA is desired to be induced in the respiratory organ, via the gastrointestinal mucosa when IgA is desired to be induced in the digestive organ, and via the genital mucosa when IgA is desired to be induced in the genital organ. On the other hand, use of the vaccine adjuvant according to the present invention make it possible to induce antigen-specific IgA antibodies in mucosal tissues even when the antigen is administered into the muscle, which is not mucosal tissue, and simultaneous induction of antigen-specific IgG antibodies can be additionally provided.

Next, the difficulty of inducing the systemic immune response by administering a vaccine on the mucous membrane will be explained. In general, the efficiency of induction of the immune response is low on the mucosal tissue in the comparison between administering vaccine on the mucous membrane and administering vaccine on the non-mucosal tissue. A cause of this is the difficulty of having an antigen efficiently permeate through the mucous membrane to reach internal dendritic cells. Further causes of this include the facts that the epithelial layer serves as a physical barrier at the surface of the mucous membrane (e.g., a layer with small gaps is formed by strong bond between epithelial cells), that the antigen is diffused by the mucus having high fluidity, that the antigen is degraded by digestive enzymes, and the like. Intranasal immunization of conventional vaccines is often performed because the nasal mucosa is relatively thin in comparison with other mucous membranes, but the efficiency of the induction of immunity is still not sufficient. As one of the means to overcome the problem, for example, a bacterial toxin that disrupts the epithelial layer can be used as an adjuvant, but this may damage the nerve in the case of intranasal immunization to cause olfactory impairment (because olfactory bulbs are near) and the face paralysis. Moreover, one of other causes is that the mechanism for inducing immunological unresponsiveness (immune tolerance) to antigens is developed in the mucosal tissue. The mucous membranes in the nasal cavity or the intestinal tract are exposed to a wide variety of exogenous antigens every day and negative responses to them are usually maintained. In particular, the gastrointestinal tract has a system of oral immune tolerance and has a mechanism of strongly suppressing the immunity to foods. Therefore, oral vaccines do not activate the immunity but suppress it to the contrary. On the other hand, the defense response is induced when a pathogen enters the body because body components of the pathogen activate innate immune receptors and induce inflammation and remove the negative responses. Therefore the combination with a conventional adjuvant that activates an innate immune receptor is tried to increase the efficiency of induction of the immune response. However, the effect is not sufficient in comparison with the immunity induced by intramuscular injection involving direct injection of an antigen into the body with the problem of permeability described above.

Ways to overcome the obstacles described above when the adjuvant for vaccine according to the present invention is administered by intramuscular injection will be described. Adjuvants have conventionally been used in combination sometimes for the purpose of activating dendritic cells to increase the efficiency of induction of the immune response, but the main purpose of that is to enhance the Th1 response effective for removing the infecting pathogens. As described above, dendritic cells in non-mucosa tissues usually have no function of IgA induction and the idea to use an adjuvant in combination for the purpose of conferring the function of IgA induction on such dendritic cells has not been known. What is remarkable in the present invention in addition to this idea is administration of the antigen onto the mucous membrane surface to be performed in addition to the immunization by intramuscular injection. By using the combination of a Dectin-1 ligand, which converts dendritic cells into the mucosal type and a TLR agonist, which activates dendritic cells, the systemic immune response including the strong antigen-specific Th1 response as well as antigen-specific IgA-producing memory cells and antigen-specific Th17 cells can be induced and transferred to the mucous membrane in the whole body. Moreover, by subsequently loading at least the antigen onto the mucous membrane surface desired to have the IgA induction to obtain a higher antibody titer of antigen-specific IgA, a higher dose of antigen-specific IgA can be induced. In the conventional process, loading only an antigen onto the mucous membrane with no immunization hardly results in the acquisition of immunity, but immune tolerance is induced to the contrary. However, since a certain amount of IgA memory cells have been induced in the whole body by the immunization by intramuscular injection, they are explosively increased by the subsequent booster immunization and produce IgA. Meanwhile, IgG and the Th1 response are also induced by use of an adjuvant that activates the systemic immune system, such as conventional use of a single TLR agonist, but IgA memory cells are not produced unless a Dectin-1 ligand is used in combination like the present invention.

As described above, the adjuvant for vaccine and the method for inducing immunity according to the present invention are innovative creations devised based on the knowledge of the properties of the dendritic cells that reside in the mucous membrane and details of the mucosal immune response including the knowledge that in the presence of memory IgA, IgA-producing cells rapidly proliferate upon the antigen loading and induce a high dose of IgA and can acquire all the advantages of the conventional immunization by intramuscular injection and the mucosal immunity.

As used herein, the term "adjuvant" means a substance that is administered with an antigen and thereby increases the antigenicity of the antigen to facilitate the induction of immune response. In the present invention, a Dectin-1 ligand, which will be described in detail below, and a TLR agonist are used as an adjuvant. The adjuvant for vaccine may be a composition containing the Dectin-1 ligand and the TLR agonist, but the Dectin-1 ligand and the TLR agonist may be separate from the viewpoint of storage stability of the adjuvant.

As used herein, the term "Dectin-1" refers to a receptor in dendritic cells that is a receptor specific for substances having the glucan structure represented by $\beta$-1,3-glucan. The "Raldh2 gene" is a gene whose translation product is known as an enzyme that catalyzes the synthesis of retinoic acid from retinal. Herein, the "Raldh2 gene" may be a gene from any living organism and it is known as ALDH1A2 in human. The human Raldh2 mRNA is identified by GenBank accession number: NM 001206897, the human Raldh2 protein is identified by GenBank accession number: NP_001193826, the murine Raldh2 mRNA is identified by GenBank accession number: NM_009022, and the murine Raldh2 protein is identified by GenBank accession number: NP_033048.

As used herein, the term "Dectin-1 ligand" means a substance that specifically binds to Dectin-1 and encompasses agonists binding to Dectin-1. Moreover, the Dectin-1 ligand is preferably an inducer of expression of Raldh2 since it is inferred to have an effect according to the present invention through the induction of expression of Raldh2.

As used herein, the term "inducer of expression of Raldh2" means a substance that significantly increases the expression of Raldh2 in at least dendritic cells upon the administration thereof or a composition containing the substance. As used herein, the term "expression" includes, unless specifically noticed, both concepts of transcription, by which mRNA is synthesized based on a DNA sequence, and translation, by which a protein is synthesized based on an mRNA sequence.

The inducer of expression of Raldh2 is not particularly limited as long as the expression (transcription or translation) of Raldh2 in dendritic cells is significantly increased and may be, for example, granulocyte monocyte colony stimulating factor (GM-CSF) or glucan-based compound.

As used herein, the term "glucan-based compound" refers to a substance having the glucan structure generally called glucan and is not particularly limited as long as it is a substance that provides the effect according to the present invention and examples thereof include $\beta$-1,3-glucan. The $\beta$-1,3-glucan may be any compound whose main chain has a structure in which glucose is linked via the $\beta$-1,3 linkage and may have a structure in which glucose is linked via the $\beta$1-6 linkage or the like in a side chain(s). Specific examples of $\beta$-1,3-glucan include curdlan, carboxymethylated curdlan, sizofiran, zymosan, lentinan, and the like. Among glucan-based compounds, $\beta$-1,3-glucan is preferred from the view point of acting as a Dectin-1 ligand more surely.

As used herein, the term "TLR agonist" refers to a molecule that provides, when it binds to TLR, stimulation similar to that provided when a natural ligand binds to TLR. The TLR agonists include natural ligands. As used herein, the TLR agonist may be an agonist of any TLR. A known or commercially available TLR agonist may be used.

Examples of the TLR agonist include TLR1-9 agonists. These TLR agonists exhibit a common effect in, for example, human and mouse, since TLR1-9 have homologies in them.

Examples of the TLR1 agonist include various triacyllipopeptides, functional fragments or analogs thereof, Pam3Cys-Ser-(Lys)4, and the like.

Examples of the TLR2 agonist include various lipopeptides, peptideglycan, heat shock proteins, functional fragments or analogs thereof, Pam3Cys-Ser-(Lys) 4, MALP-2, FSL-1, Hib-OMPC, and the like.

Examples of the TLR3 agonist include double strand RNA, double strand RNA analogs such as polyinosinic-polycytidylic acid (Poly(I:C)).

Examples of the TLR4 agonist include various lipopolysaccharides, heat shock proteins, fibrinogen, heparin sulfate, hyaluronic acid, and functional fragments or analogs thereof, aminoalkylglucosaminide phosphates (AGP), monophosphoryl lipid A (MPLA), RC-529, and the like.

TLR5 is known to be specifically expressed in CD11c-positive cells in the small intestine mucosa lamina propria and recognize flagellin on pathogenic bacteria to induce the immune response. Examples of the TLR5 agonist include recombinant flagellin, CBLB502, and the like.

Examples of the TLR6 agonist include various diacyllipopeptides, functional fragments or analogs thereof, FSL-1, Pam2Cys, and the like.

TLR7 recognizes single strand RNA derived from viruses and activates the innate immune system. Examples of the TLR7 agonist include Imiquimod, R-848, which is a derivative of Imiquimod, Loxoribine, Bropirimine, Gardiquimod, and the like. Imiquimod, Loxoribine, Gardiquimod, and R-848 are also known as human TLR8 agonists.

TLR9 recognizes CpG oligodeoxynucleotide (CpG ODN) derived from bacteria and viruses and activates the innate immune system in the living body. The CpG ODN refers to a short synthetic oligodeoxynucleotide containing the CpG motif. The CpG ODN can be used as a TLR9 agonist used in the adjuvant for vaccine according to the present invention, but is not limited to this. The CpG ODN to be the TLR9 agonist may be designed by those skilled in the art as appropriate and commercially available CpG ODNs may also be used. When used in the present invention, the CpG ODN may be a salt thereof and may be, for example, a sodium salt. The CpG ODN may be an unmethylated CpG ODN. Examples thereof include CpG-ODN 1668, 2006, 1826, 2395, and the like.

Among the TLR agonists, from the viewpoint of having the effect according to the present invention surely, the TLR2 agonist, the TLR4 agonist, the TLR5 agonist, the TLR7 agonist, and the TLR9 agonist, which can exhibit similar responses in cells, are preferred and the TLR7 agonist and the TLR9 agonist are more preferred. The TLR7 agonist may be a TLR8 agonist.

One aspect of the adjuvant for vaccine according to the present invention comprises incomplete Freund's adjuvant in addition to the Dectin-1 ligand and the TLR agonist. "Freund's adjuvant" is an adjuvant that forms water-in-oil emulsion and, in contrast to complete Freund's adjuvant that contains heat-killed tubercle bacillus, such an adjuvant without heat-killed tubercle bacillus is called incomplete Freund's adjuvant.

The adjuvant for vaccine according to the present invention may contain, as long as it provides the effect according to the present invention, an additional adjuvant substance(s) other than the Dectin-1 ligand and the TLR agonist. Non-limiting examples of such an adjuvant substance include sedimentary adjuvants such as aluminium hydroxide, sodium hydroxide, aluminum phosphate, calcium phosphate, alum, carboxyvinyl polymer, complete Freund's adjuvant, liquid paraffin, lanoline, Montanide ISA7 63AV, Montanide ISA51, and the like.

The adjuvant for vaccine according to the present invention is preferably an adjuvant for administering with at least one antigen to have the effect according to the present invention more surely. The antigen to be used here is similar to the antigen to be used in vaccine as described below.

(Vaccine)

The vaccine according to the present invention comprises at least one antigen in addition to the adjuvant for vaccine according to the present invention. The vaccine may be a vaccine composition containing the aforementioned adjuvant for vaccine and the aforementioned antigen, but, from the viewpoint of storage stability of the vaccine, the aforementioned adjuvant for vaccine and the aforementioned antigen may be separate.

As used herein, the term "antigens" refers to a generic term for foreign substances, or a part thereof, that enter the living body from the outside and cause the immune response in the living body. The antigens include exogenous pathogens such as bacteria and viruses that cause various infections as well as allergens, which cause the allergic reaction among pollens, foods, and the like.

Non-limiting examples of the viral antigens include an inactivated or attenuated preparation(s) of at least one virus selected from the group consisting of influenza virus, norovirus, rotavirus, human papillomavirus, varicella virus, measles virus, mumps virus, poliovirus, adenovirus, herpesvirus, human coronavirus, rubella virus, HIV, smallpox virus, Ebola virus, hepatitis virus, Japanese encephalitis virus, parvovirus, and cowpox virus, or a part or a component thereof.

Non-limiting examples of the bacterial antigens include an inactivated or attenuated preparation(s) of at least one bacterium selected from the group consisting of *Haemophilus influenzae, Streptococcus pneumoniae, Bordetella pertussis,* tetanus bacilli, *Corynebacterium diphtheriae, Tubercle bacilli, Escherichia coli* such as enterohemorrhagic *Escherichia coli, Vibrio cholerae,* salmonellae, and methicillin-resistant *Staphylococcus aureus* or a part or a component thereof.

Non-limiting examples of the allergens include pollen (cedar pollen, Poaceae pollen, Compositae pollen, and the like), fungi, insects, foods (soybean, egg, milk, and the like), and drugs (penicillin and the like).

The vaccine according to the present invention induces the mucosal immune response represented by the antigen-specific IgA antibody production and the Th17 response in addition to the systemic immune response represented by the antigen-specific IgG antibody production and the Th1 response. Whether the mucosal immune response has been induced or not can be confirmed by a known in vitro or in vivo method. For example, in an in vivo method, the mucosal immune response can be determined to be induced if the amount of serum or fecal antigen-specific IgA antibodies is measured by ELISA or the like and the amount of the antibodies is increased. Moreover, in an in vitro method, the mucosal immune response can be determined to be induced if for example, IgA antibody-producing cells such as Peyer's patch cells are cultured, the amount of antigen-specific IgA antibodies contained in the culture supernatant is measured by ELISA or the like, and the amount of the antibodies is increased.

Whether the systemic immune response has been induced or not can also be confirmed by a known in vitro or in vivo method. For example, in an in vivo method, the systemic immune response can be determined to be induced if the amount of serum antigen-specific IgG antibodies is measured by ELISA or the like and the amount of the antibodies is increased.

The vaccine according to the present invention may be administered in any mode as long as the systemic immune response and the mucosal immune response can be induced and it can be administered, for example, in a mode selected from the group consisting of transdermal administration, subcutaneous administration, intradermal administration, and intramuscular administration. The systemic Th1 response and the IgG antibody production are induced more efficiently by administering the vaccine in a mode selected from the group consisting of transdermal administration, subcutaneous administration, intradermal administration, and intramuscular administration. Among these, the vaccine is preferably administered by intramuscular administration. As used herein, the intramuscular administration is a concept that encompasses the terms such as intramuscular injection, i.m. injection, administration by intramuscular injection, and immunization by intramuscular injection.

As illustrated by Examples as described below, after the administration of the vaccine according to the present invention, the antigen-specific IgG antibody production lasts for a long period of time (at least 10 weeks) and the antigen-specific IgA antibody production lasts to the extent that it reaches its peak 2 to 3 weeks after the administration. Moreover, the present inventors found that the production of a very high titer of antigen-specific IgA antibodies can be maintained further for about 3 months by performing booster immunization involving administering only the antigen onto the mucous membrane surface a certain period of time after the vaccine administration and the antigen-specific IgA antibody production can be restored repeatedly and maintained by repeating the booster immunization involving administering at least the antigen onto various mucous membrane surfaces. They also found that the strong antigen-specific Th17 response can be induced on the mucous membrane surface by the administration of the antigen in the booster immunization.

In the present invention, use of a combination of a Dectin-1 ligand and a TLR agonist in dendritic cells as an adjuvant induces the systemic Th1 response and the IgG antibody production and the Th17 response in the mucous membrane and the IgA antibody production and booster immunization via a selected administration route can re-induce the Th17 response and the IgA antibody production in a desired mucous membrane, such as those of the intestinal tract and the respiratory tract and both of the entry of the pathogen and aggravation of the disease condition can be prevented effectively.

As used herein, the "booster immunization involving administering an antigen" may involve administering the antigen in any mode as long as it is possible to restore and maintain the IgA antibody production and examples of the mode of administration include modes of administration involving direct application onto the mucous membranes, such as oral administration, intranasal administration, transmucosal administration, transvaginal administration, ophthalmic administration, or intrarectal administration. The Th17 response and the IgA antibody production can be induced more efficiently on the desired mucous membrane such as those of the intestinal tract and the respiratory tract by the administration in a mode of administration involving the direct application onto the mucous membrane and it can be administered to the subject more easily by the administration by oral administration.

In the booster immunization involving administering an antigen, the antigen may be administered by using no adjuvant or the antigen may be administered with an adjuvant(s).

For example, it has been confirmed, as illustrated by Examples as described below, that the antigen-specific IgA production in the lung can be induced by performing booster immunization by intranasal administration and the antigen-specific IgA production in the gastrointestinal tract is induced by performing booster immunization by oral administration. In addition, it is considered that vaccine for human papillomavirus, which causes uterine cervix cancer, will be administered by transvaginal administration to prevent the infection.

The length of time from the vaccine administration to the booster immunization involving administering only the antigen is not particularly limited and the length may be, for example, 3 weeks, 2 to 3 months, 1 year, several years, or the like. If the vaccine is administered once, then the booster immunization may be performed subsequently any time when the mucosal immune response is desired to be induced.

For example, when influenza virus is used as an antigen, the infection of the influenza virus itself can be suppressed by the mucosa immunity by administering a vaccine containing several antigens beforehand and performing booster immunization prior to the season when influenza is prevalent every year with an antigen expected to be prevalent in the year.

(Method for Inducing Immunity)

The present invention encompasses the method for inducing immunity comprising a step of administering the vaccine according to the present invention. Moreover, the present invention encompasses a method for inducing immunity, further comprising a step of administering an antigen a certain period of time after the step of administering a vaccine to perform at least once of booster immunization.

(Method for Prevention)

The present invention also encompasses a method for preventing a viral infection or a bacterial infection, comprising a step of administering a vaccine comprising at least one antigen derived from virus or bacterium and an adjuvant for vaccine comprising a Dectin-1 ligand and a TLR agonist. Moreover, the present invention also encompasses a method for preventing a viral or bacterial infection, further comprising a step of administering an antigen a certain period of time after the step of administering a vaccine to perform booster immunization.

The "method for prevention" means a method for preventing an infection or an allergic reaction caused by an antigen before its onset.

(Method for Treatment)

As used herein, the term "vaccine" refers to a pharmaceutical preparation used for the purpose of the prevention of infection and contains a deactivated or attenuated antigen. The vaccine can induce the immune response when administered to an animal such as a human and prevent the infection with the antigen contained in the vaccine and the aggravation of the infection after the induction.

The present invention also encompasses a method for treating a viral infection or a bacterial infection, comprising a step of administering an inducer of immunity comprising a Dectin-1 ligand and a TLR agonist to a subject infected with a viral or bacterial infection. Moreover, the present invention also encompasses a method for treating a viral infection or bacterial infection, further comprising a step of administering an antigen a certain period of time after the step of administering an inducer of immunity to perform booster immunization.

The "method for treatment" means a method for treating an infection or an allergic reaction caused by an antigen after its onset.

In the method for inducing immunity, the method for prevention, and the method for treatment described above, the step of administering a vaccine may be of administering the vaccine in any mode as long as the systemic immune response and the mucosal immune response can be induced and the vaccine can be administered, for example, in a mode selected from the group consisting of transdermal administration, subcutaneous administration, intradermal administration, and intramuscular administration. By administering the vaccine in a mode selected from the group consisting of transdermal administration, subcutaneous administration, intradermal administration, and intramuscular administration, the systemic Th1 response and the IgG antibody production are induced more efficiently. Among them, it is preferred to administer the vaccine by intramuscular administration.

In the method for inducing immunity, the method for prevention, and the method for treatment described above, "after a certain period of time" may be any time after the disappearance of the induction of IgA antibody production by the administration of the first vaccine. For example, it may be 3 weeks, 2 to 3 months, 1 year, or several years after the administration of the vaccine and the booster immunization may be performed when the mucosal immune response is desired to be induced.

In the method for inducing immunity, the method for prevention, and the method for treatment described above, the step of administering an antigen to perform at least once of booster immunization may be of administering the antigen in any mode as long as it is possible to restore and maintain the IgA antibody production and examples of the mode of administration include modes of administration involving direct application onto the mucous membranes, such as oral administration, intranasal administration, transmucosal administration, transvaginal administration, ophthalmic administration, intrarectal administration, or the like. The Th17 response and the IgA antibody production can be induced more efficiently on the desired mucous membrane such as those of the intestinal tract and the respiratory tract by the administration in a mode of administration involving the direct application onto the mucous membrane and it can be administered to the subject more easily by the administration by oral administration.

In the step of administering an antigen to perform at least once of booster immunization, the antigen may be administered or the antigen may be administered with an adjuvant.

The disclosure of all Patent Literature and Non-Patent Literature cited herein is incorporated herein by reference in their entirety.

Examples

The present invention will be specifically described below based on Examples, but the present invention is not limited to this. Those skilled in the art can modify the present invention into various aspects without departing from the spirit of the present invention and such modifications are also included within the scope of the present invention.

1. Induction of IgA by Spleen-Derived Classical Dendritic Cells ("Spleen cDCs") Stimulated with GM-CSF Spleen cDCs were stimulated for 24 hours using ovalbumin (OVA; 100 µg/ml) as an antigen and CpG ODN 1668 (1 µg/ml) only or the combination of CpG ODN and GM-CSF (10 ng/ml) as an adjuvant.

Here, the fractioning of murine small intestine mucosa lamina propria cells with the dendritic cell marker CD11c and the macrophage marker CD11b produces the 4 groups: R1 (dendritic cells) (CD11c high CD11b low), R2 (dendritic cells) (CD11c high CD11b high), R3 (macrophages) (CD11c int CD11b int), R4 (acidophiles) (CD11c int CD11b high). The R2 dendritic cells specifically express Raldh2 and induce the Th17 response and the IgA production (Non-Patent Literature 1). Therefore, the R2 dendritic cells were stimulated with OVA (100 µg/ml) and CpG ODN 1668 (1 µg/ml) as positive control. Spleen cDCs were stimulated with OVA (100 µg/ml) and CpG ODN 1668 (1 µg/ml) with or without GM-CSF (10 ng/ml).

On Day 0 and Day 14 after the stimulation, dendritic cells (each $5\times10^4$ cells) (or PBS) which took up the antigen were intraperitoneally administered into CD57BL/6 mice. On Day 21 to Day 25, 1 mg/mouse of OVA was orally administered daily and, on Day 32, total of antigen-specific IpG in serum and antigen-specific IgA in feces were measured by ELISA.

The summary and the results of the experiment are illustrated in FIG. 1. Stimulation of spleen cDCs (SPDC in the figure) with OVA and only CpG ODN induced little production of IgA, but addition of GM-CSF (SPDC+GM-CSF in the figure), which is known to induce the expression of Raldh2, induced IgA production more than the R2 dendritic cells (LPDC in the figure) did.

2. Induction of Raldh2 Expression in Spleen cDCs by Glucan

Next, zymosan (component of yeast cell wall of *Saccharomyces cerevisiae;* 25 ng/ml) and curdlan (($\beta$-1,3-glucan derived from *Agrobacterium* spp., *Alcaligenes* spp.; 25 ng/ml) were used as glucan-based compound. Spleen cDCs were stimulated with these substances for 24 hours and, after collecting RNA, the expression of Raldh2 mRNA was measured by RT-PCR.

The summary and the results of the experiment are illustrated in FIG. 2. Curdlan and zymosan induced the expression of Raldh2 in spleen cDCs like GM-CSF.

3. Gastrointestinal Tract-Specific IgA Induction by Immunization (Intramuscular Injection) with CpG ODN+Curdlan 200 µl/mouse of an IFA emulsion in which OVA (500 µg/ml) as an antigen and CpG ODN 1668 (5 µg/ml) and/or curdlan (5 mg/ml) as an adjuvant were added to incomplete Freund's adjuvant (IFA) was administered by intramuscular injection. Subsequently, sera and feces were harvested over time (once a week) and total of antigen (OVA)-specific IpG in serum and antigen-specific IgA in feces were measured by ELISA.

The summary and the results of the experiment are illustrated in FIG. 3. Using any of the adjuvants, other than control containing no OVA, antigen-specific IgG was induced and this state lasted for at least 7 weeks. In contrast, IgA was induced only when both of CpG ODN and curdlan were administered.

4. Cholera Toxin (CT)-Specific IgA Induction by Immunization (Intramuscular Iinjection) with CpG ODN+Curdlan Next, an experiment similar to 3. was conducted by using CT (1 µg/mouse) as the antigen. 3 weeks after the immunization by intramuscular injection, total of antigen-specific IpG in serum and antigen-specific IgA in feces were measured by ELISA.

The summary and the results of the experiment are illustrated in FIG. 4. As illustrated in the left panel in the figure, IgG was induced at equal levels with IFA plus CT and these with CpG ODN and curdlan added. In contrast, IgA was induced at markedly higher level than that with IFA plus CT when CpG ODN and curdlan were added.

5. Amelioration of Diarrhea Caused by CT with Immunization (Intramuscular Injection) with CpG ODN+Curdlan After the experiment of 4., 20 µg of CT was orally administered to mice and symptoms of the diarrhea were examined. The summary and the results of the experiment are illustrated in FIG. 5. In the normal intestine, solid stool was found and the appendix was also small. Meanwhile, with administration of IFA only or IFA plus CT only, liquid stool and the enlargement of the appendix were observed. In contrast, in the mice to which IFA, CT, CpG ODN and curdlan were administered, solid stool and no enlargement of the appendix were found.

6. Effect of Booster Immunization with Only Antigen After Immunization (Intramuscular Injection) of CpG ODN+Curdlan (1)

After the immunization of mice by intramuscular injection with IFA to which OVA and CpG ODN and/or curdlan or neither of them were added, on Day 42, a single dose of 1 mg/mouse of OVA was orally administered to perform booster immunization, and, on the day of the oral administration and 1 week later, antigen-specific fecal IgA was measured by ELISA and antigen-specific IgA-producing cells were measured by ELISpot.

The summary and the results of the experiment are illustrated in FIG. 6. In either case, IgG production was induced and the effect was maintained over before and after the booster immunization. Meanwhile, IgA was hardly detected on the day of oral administration of OVA, but, 1 week after the booster immunization, antigen-specific IgA production was induced at a markedly higher level when the adjuvant contained both of CpG ODN and curdlan in comparison with the level when other adjuvants were used. Antigen-specific IgA-producing cells were also markedly increased when both of CpG ODN and curdlan were contained in comparison with those when other adjuvants were used.

7. Effect of Booster Immunization with Only Antigen After Immunization (Intramuscular Injection) of CpG ODN+Curdlan (2)

After conducting an experiment similar to 6., total of antigen-specific IpG in serum and antigen-specific IgA in feces were measured over time for a further extended period of time. The summary and the results of the experiment are illustrated in FIG. 7. The amount of antigen-specific IgG hardly decreased for the next 13 weeks after the booster immunization and, on the 13th week, the slight reduction was recovered to the original level by second booster immunization. Meanwhile, the amount of fecal antigen-specific IgA gradually decreased and was almost zero in the 13th week. But, on the 13th week, it was markedly recovered by second booster immunization with a single dose oral administration of 1 mg/mouse of OVA.

8. Effect of Booster Immunization with Only Antigen After Immunization (Intramuscular Injection) of CpG ODN+Curdlan (3)

7 days after conducting an experiment similar to 6. and booster immunization by OVA oral administration, spleen and intestinal mucosa lamina propria cells were extracted from the mice and cultured in the presence of the antigen (OVA 100 µg/ml), and, 4 days later, production of IFN-γ, IL-4, and IL-17 was measured by ELISA.

The summary and the results of the experiment are illustrated in FIG. 8. As illustrated, it was confirmed that in the intestinal mucosa lamina propria cells, the IFN-γ and IL-17 production were induced when the adjuvant contained curdlan and CpG ODN, and the Th1 and Th17 responses were induced in the gastrointestinal tract by booster immunization by oral administration of OVA. Meanwhile, IL-4 was not induced and it was considered that the Th2 response was not induced.

9. Effect of Booster Immunization with Only Antigen After Immunization (Intramuscular Injection) of CpG ODN+Curdlan (4)

IFA, IFA+OVA+CpG ODN, IFA+OVA+curdlan, and IFA+OVA+CpG ODN+curdlan were administered to mice by intramuscular injection, respectively. On Day 35, 1 µg/mouse of OVA was administered by intranasal administration to perform booster immunization, and, 7 days later antigen-specific total IgG in the serum and IgA in the bronchoalveolar lavage fluid were measured by ELISA.

The summary and the results of the experiment are illustrated in FIG. 9. It was confirmed that, when the adjuvant contains both of CpG and curdlan, the antigen-specific IgA production in the lungs can be induced by booster immunization by intranasal administration of OVA.

10. Effect of Booster Immunization with Only Antigen After Immunization (Intramuscular Injection) of CpG ODN+Curdlan (5)

In the experiment of 9, 7 days after the intranasal administration of OVA, pulmonary mucosa lamina propria cells were extracted from the mice and cultured in the presence of the antigen (OVA 100 µg/ml) for 4 days and IFN-γ, IL-4, and IL-17 production was measured by ELISA.

The summary and the results of the experiment are illustrated in FIG. 10. It was confirmed that the IFN-γ production is induced when the adjuvant contains at least one of CpG ODN and curdlan, and the Th1 response is induced in the lung. Meanwhile, it was confirmed that the IL-17 production is induced at a markedly higher level when the adjuvant contains both of CpG ODN and curdlan, and the Th17 response is strongly induced when this combination is used as an adjuvant. Meanwhile, IL-4 was not induced and it was considered that the Th2 response was not induced (data not shown).

11. Effect of Booster Immunization with Only Antigen After Immunization (Intramuscular Injection) of CpG ODN+Curdlan (6)

OVA only, OVA and CpG ODN, OVA and curdlan, or OVA and CpG ODN and curdlan were added to IFA and each of them was administered to mice by intramuscular injection (Day 0). On Day 35, 2 mg per mouse of Medroxyprogesterone was subcutaneously administered. On Day 42, 100 µg per mouse of OVA was intravaginally administered and antigen-specific IgA in the vaginal lavage fluid was measured by ELISA 1 week later.

The result of the experiment is illustrated in FIG. 11. It was confirmed that, when the adjuvant contains both of CpG and curdlan, the antigen-specific IgA production in the vagina can be induced by booster immunization by intravaginal administration of OVA.

12. Enhancement of Expression of Dectin-1 in Spleen cDCs by CpG ODN Stimulation

Next, the expression of Dectin-1, which is a receptor that recognizes β-1,3-glucan, in dendritic cells was measured. The summary and the result of the experiment are illustrated in FIG. 12. As illustrated in the left panel in the figure, it was confirmed that, in spleen-derived dendritic cells, the expression of Dectin-1 is not high, but the expression of Dectin-1 increases more than 3 times by stimulating the cells with CpG ODN. Dectin-1 is known to induce the Th17 response. These indicate the mechanism of the present invention in which the addition of both of CpG ODN and β-1,3-glucan to the adjuvant makes dendritic cells easy to receive the stimulation with β-1,3-glucan and induces the Th17 response.

13. Effect of Immunization (Intramuscular Injection) with R-848+Curdlan and Booster Immunization with Antigen IFA, IFA+OVA+R-848 (100 µg/mouse), or IFA+OVA+R-848+curdlan were intramuscularly administered to mice. 28 days later, a single dose of 1 mg/mouse of OVA was orally administered to give booster immunization and total of antigen-specific IpG in serum and antigen-specific IgA in feces were measured by ELISA over time. R-848 is a TLR7/8 agonist.

The summary and the results of the experiment are illustrated in FIG. 13. In either case, the antigen-specific IgG production was induced, and the effect lasted until the 5th week. Meanwhile, the IgA production reached a peak in the 3rd week after the intramuscular injection and then decreased, but booster immunization in the 4th week induced the IgA production to a considerably higher level than that of the first peak.

14. Gastrointestinal Tract-Specific IgA Induction by Immunization (Intramuscular Injection) with CpG ODN+Lentinan 200 µl/mouse of an IFA emulsion in which OVA (500 µg/ml) as an antigen and CpG ODN 1668 (5 µg/ml) and/or lentinan (5 mg/ml) as an adjuvant were added to IFA was administered to mice by intramuscular injection. Subsequently, sera and feces are harvested over time and total of antigen-specific IpG in serum and antigen-specific IgA in feces were measured by ELISA.

The summary and the results of the experiment are illustrated in FIG. 14. Using any of the adjuvants, other than control containing no OVA, antigen-specific IgG was induced and this state lasted for at least 5 weeks. Meanwhile, IgA was induced only when the adjuvant contains both of CpG ODN and lentinan and this induction was rapidly disappeared after having reaching a peak in the 3rd week.

15. Effect of Booster Immunization with Only Antigen After Immunization (Intramuscular Injection) of CpG ODN+Lentinan (1)

After the immunization of mice by intramuscular injection with IFA to which OVA and CpG ODN and/or lentinan or neither of them were added, on Day 42, a single dose of 1 mg/mouse of OVA was orally administered to give booster immunization, and, on the day of the oral administration and 1 week later, antigen-specific fecal IgA was measured by ELISA and antigen-specific IgA-producing cells were measured by ELISpot.

The summary and the results of the experiment are illustrated in FIG. 15. In either case, IgG production was induced and the effect was maintained over before and after the booster immunization. Meanwhile, IgA was hardly detected on the day of oral administration of OVA, but, 1 week after the booster immunization, antigen-specific IgA production was induced at a markedly higher level when the adjuvant contained both of CpG ODN and lentinan in comparison with the level when other adjuvants were used. Antigen-specific IgA-producing cells were also markedly increased when both of CpG ODN and lentinan were contained in comparison with those when other adjuvants were used.

16. Effect of Booster Immunization with Only Antigen After Immunization (Intramuscular Injection) of CpG ODN+Lentinan (2)

An experiment similar to 15. was conducted. On Day 7 after booster immunization by OVA oral administration, spleen and intestinal mucosa lamina propria cells were extracted from the mice and cultured in the presence of the antigen (OVA 100 µg/ml) and 4 days later, IFN-γ, IL-4, and IL-17 production was measured by ELISA.

The summary and the results of the experiment are illustrated in FIG. 16. As illustrated, it was confirmed that in the intestinal mucosa lamina propria cells, the IFN-γ and IL-17 productions are induced when the adjuvant contains lentinan and CpG ODN and the Th1 and Th17 responses are induced in the gastrointestinal tract by booster immunization by oral administration of OVA. In either tissue, IL-4 was not induced and it was considered that the Th2 response was not induced.

17. Gastrointestinal Tract-Specific IgA Induction by Immunization (Intramuscular Injection) with CpG ODN+Curdlan in Dectin-1 Deficient Mice 200 µl/mouse of an IFA emulsion in which OVA (500 µg/ml) as an antigen and CpG ODN 1668 (5 µg/ml) and curdlan (5 mg/ml) as an adjuvant were added to IFA was administered to Dectin-1 heterodeficient mice (Clec7a +/−) and Dectin-1 homodeficient mice (Clec7a −/−) by intramuscular injection. 3 weeks later, sera and feces are harvested and total of antigen-specific IpG in serum and antigen-specific IgA in feces were measured by ELISA.

The summary and the results of the experiment are illustrated in FIG. 17. Antigen-specific IgG was induced in both of the Dectin-1 heterodeficient mice and the Dectin-1 homodeficient mice. Meanwhile, IgA was not detected in the Dectin-1 homodeficient mice, while it was detected in the Dectin-1 heterodeficient mice.

18. Effect of Booster Immunization with Only Antigen After Immunization (Intramuscular Injection) of CpG ODN+Curdlan in Dectin-1 Deficient Mice (1)

After immunization of Dectin-1 heterodeficient mice and Dectin-1 homodeficient mice with IFA to which OVA and CpG ODN and curdlan were added by intramuscular injection, on Day 42, a single dose of 1 mg/mouse of OVA was orally administered to perform booster immunization, and, on the day of the oral administration and, 1 week later, antigen-specific fecal IgA was measured by ELISA.

The summary and the results of the experiment are illustrated in FIG. 18. In either mouse, IgG production was induced and the effect was maintained over before and after the booster immunization. Meanwhile, IgA was hardly detected in either mouse on the day of oral administration of OVA, but, 1 week after the booster immunization, whereas the antigen-specific IgA production in Dectin-1 heterodeficient mice was induced to a markedly high level, the induction of the IgA production in Dectin-1 homodeficient mice was markedly reduced.

19. Effect of Booster Immunization with Only Antigen After Immunization (Intramuscular Injection) of CpG ODN+Curdlan in Dectin-1 Deficient Mice (2)

An experiment similar to 18. was conducted. On Day 7 after booster immunization by OVA oral administration, spleen and intestinal mucosa lamina propria cells were extracted from the mice and cultured in the presence of the antigen (OVA 100 µg/ml) and 4 days later, IFN-γ, IL-4, and IL-17 production was measured by ELISA.

The summary and the results of the experiment are illustrated in FIG. 19. As illustrated, it was confirmed that, in the intestinal mucosa lamina propria cells in Dectin-1 heterodeficient mice, the IFN-γ and IL-17 productions were induced and by booster immunization by oral administration of OVA, the Th1 and Th17 responses were induced in the gastrointestinal tract. However, both of the IFN-γ and IL-17 productions were markedly reduced in the Dectin-1 homodeficient mice. In either tissue, IL-4 was not induced and it was considered that the Th2 response was not induced.

INDUSTRIAL APPLICABILITY

The adjuvant for vaccine according to the present invention is useful in industry as an adjuvant for vaccine used against various infections caused by exogenous pathogens such as bacteria and viruses as well as allergic reactions caused by pollen and foods as an allergen.

The invention claimed is:

1. A method for inducing a mucosal immune response in a subject or antigen-specific IgA production in the mucosa of the subject, comprising
   inducing the mucosal immune response or the antigen-specific IgA production in the mucosa by administering to the subject by intramuscular injection a vaccine which comprises
   at least one antigen and
   an adjuvant for vaccine comprising a Dectin-1 ligand and a TLR agonist.

2. The method according to claim 1, further comprising administering to the subject a booster vaccine, which comprises an antigen, a certain period of time after the step of administering a vaccine.

3. The method according to claim 2, wherein administration of the booster vaccine is by oral administration, intranasal administration, transmucosal administration, transvaginal administration, ophthalmic administration, or intrarectal administration.

4. The method according to claim 2, wherein the booster vaccine is administered without any adjuvant.

5. The method according to claim 1, wherein the Dectin-1 ligand is an inducer of expression of a Raldh2 gene.

6. The method according to claim 5, wherein the inducer of expression of a Raldh2 gene is granulocyte monocyte colony stimulating factor (GM-CSF) or a glucan-based compound.

7. The method according to claim 1, further comprising an incomplete Freund's adjuvant.

8. The method according to claim 1, wherein the at least one antigen is an inactivated or attenuated virus or a part thereof or a component thereof, an inactivated or attenuated bacterium or a part thereof or a component thereof, or an allergen.

9. The method according to claim 1, wherein the vaccine induces antigen-specific IgA production.

10. The method according to claim 1, wherein the vaccine induces antigen-specific IgA production and antigen-specific IgG production.

* * * * *